US009155626B2

(12) United States Patent
Huebner et al.

(10) Patent No.: US 9,155,626 B2
(45) Date of Patent: Oct. 13, 2015

(54) RADIAL HEAD PROSTHESIS WITH FLOATING ARTICULAR MEMBER

(71) Applicant: Acumed LLC, Hillsboro, OR (US)

(72) Inventors: Randall J. Huebner, Portland, OR (US); Jeff Andrew Bergquist, Portland, OR (US); Kara J. Budor, Portland, OR (US); Larry W. Ehmke, Beaverton, OR (US)

(73) Assignee: ACUMED LLC, Hillsboro, OR (US)

( * ) Notice: Subject to any disclaimer, the term of this patent is extended or adjusted under 35 U.S.C. 154(b) by 63 days.

(21) Appl. No.: 14/023,179

(22) Filed: Sep. 10, 2013

(65) Prior Publication Data

US 2014/0074246 A1 Mar. 13, 2014

Related U.S. Application Data

(60) Provisional application No. 61/699,070, filed on Sep. 10, 2012.

(51) Int. Cl.
*A61F 2/38* (2006.01)
*A61F 2/30* (2006.01)

(52) U.S. Cl.
CPC ....... *A61F 2/3804* (2013.01); *A61F 2002/3038* (2013.01); *A61F 2002/30362* (2013.01); *A61F 2002/30364* (2013.01);
(Continued)

(58) Field of Classification Search
CPC .............. A61F 2002/3809; A61F 2002/3818; A61F 2002/3827; A61F 2/3804
USPC ............................ 623/20.11, 11–20.13, 23.42
See application file for complete search history.

(56) References Cited

U.S. PATENT DOCUMENTS 807,473 A 12/1905 Kolar
2,696,817 A 12/1954 Prevo
(Continued)

FOREIGN PATENT DOCUMENTS

DE 2545821 A1 4/1976
DE 2550704 A1 5/1976
(Continued)

OTHER PUBLICATIONS

Sulzer Medica, Sulzer Orthopedics Joint and Fracture Care Anatomical Shoulder Flyer, 2000.
Sulzer Medica, Sulzer Orthopedics Joint Care/Fracture Care Anatomical Shoulder Product Guide, 2000.
Ushio, The Journal of Bone & Joint Surgery, Partial hemiarthroplasty for the treatment of osteonecrosis of the femoral head, 2003.
(Continued)

*Primary Examiner* — David H Willse
*Assistant Examiner* — Javier Blanco
(74) *Attorney, Agent, or Firm* — Kolisch Hartwell, P.C.

(57) ABSTRACT

System, including apparatus, methods, and kits, for replacement of the proximal end of a radial bone with a prosthesis having a floating articular member. The prosthesis may include a head portion connected or connectable to a stem portion. While the stem portion remains operatively connected to the head portion, the head portion and/or an articular member thereof may be permitted to float in position relative to the stem portion. The head portion/articular member may float transversely (e.g., translationally) and/or rotationally with respect to the stem portion. The articular member may articulate with a humeral bone or both a humeral bone and an ulnar bone. In some embodiments, the head portion may include a fixed member for articulation with an ulnar bone and a floating member for articulation with a humeral bone.

12 Claims, 14 Drawing Sheets

(52) U.S. Cl.
CPC .......... *A61F 2002/30369* (2013.01); *A61F 2002/30378* (2013.01); *A61F 2002/30507* (2013.01); *A61F 2002/30563* (2013.01); *A61F 2002/30571* (2013.01); *A61F 2002/30616* (2013.01); *A61F 2002/30878* (2013.01); *A61F 2002/3809* (2013.01); *A61F 2002/3818* (2013.01); *A61F 2002/3827* (2013.01)

(56) References Cited

U.S. PATENT DOCUMENTS

| | | |
|---|---|---|
| 3,103,926 A | 9/1963 | Cochran et al. |
| 3,656,186 A | 4/1972 | Dee |
| 3,708,805 A | 1/1973 | Scales et al. |
| 3,748,662 A | 7/1973 | Helfet |
| 3,772,709 A | 11/1973 | Swanson |
| 3,774,244 A | 11/1973 | Walker |
| 3,816,854 A | 6/1974 | Schlein |
| 3,852,831 A | 12/1974 | Dee |
| 3,919,725 A | 11/1975 | Swanson et al. |
| 3,934,272 A | 1/1976 | Wearne et al. |
| 3,939,496 A | 2/1976 | Ling et al. |
| 3,990,117 A | 11/1976 | Pritchard et al. |
| 4,000,525 A | 1/1977 | Klawitter et al. |
| 4,007,494 A | 2/1977 | Sauer |
| 4,007,495 A | 2/1977 | Frazier |
| 4,008,495 A | 2/1977 | Cavendish et al. |
| 4,021,864 A | 5/1977 | Waugh |
| 4,034,418 A | 7/1977 | Jackson et al. |
| 4,038,704 A | 8/1977 | Ring |
| 4,057,858 A | 11/1977 | Helfet |
| 4,059,854 A | 11/1977 | Laure |
| 4,064,568 A | 12/1977 | Grundei et al. |
| 4,079,469 A | 3/1978 | Wadsworth |
| 4,085,466 A | 4/1978 | Goodfellow et al. |
| 4,106,130 A | 8/1978 | Scales |
| 4,129,902 A | 12/1978 | Harmon |
| 4,131,956 A | 1/1979 | Treace |
| 4,166,292 A | 9/1979 | Bokros |
| 4,187,559 A | 2/1980 | Grell et al. |
| 4,206,517 A | 6/1980 | Pappas et al. |
| 4,215,439 A | 8/1980 | Gold et al. |
| 4,216,549 A | 8/1980 | Hillberry et al. |
| 4,219,893 A | 9/1980 | Noiles |
| 4,224,695 A | 9/1980 | Grundei et al. |
| 4,242,758 A | 1/1981 | Amis et al. |
| 4,259,072 A | 3/1981 | Hirabayashi et al. |
| 4,268,920 A | 5/1981 | Engelbrecht et al. |
| 4,280,231 A | 7/1981 | Swanson |
| 4,285,070 A | 8/1981 | Averill |
| 4,293,963 A | 10/1981 | Gold et al. |
| 4,301,552 A | 11/1981 | London |
| 4,309,778 A | 1/1982 | Buechel et al. |
| 4,340,978 A | 7/1982 | Buechel et al. |
| 4,353,136 A | 10/1982 | Polyzoides et al. |
| 4,378,607 A | 4/1983 | Wadsworth |
| 4,383,337 A | 5/1983 | Volz et al. |
| 4,384,373 A | 5/1983 | Sivash |
| 4,462,120 A | 7/1984 | Rambert et al. |
| 4,470,158 A | 9/1984 | Pappas et al. |
| 4,502,160 A | 3/1985 | Moore et al. |
| 4,521,924 A | 6/1985 | Jacobsen et al. |
| 4,538,306 A | 9/1985 | Dörre et al. |
| 4,550,450 A | 11/1985 | Kinnett |
| 4,553,273 A | 11/1985 | Wu |
| 4,662,889 A | 5/1987 | Zichner et al. |
| 4,728,332 A | 3/1988 | Albrektsson |
| 4,743,261 A | 5/1988 | Epinette |
| 4,822,364 A | 4/1989 | Inglis et al. |
| 4,892,546 A | 1/1990 | Kotz et al. |
| 4,919,671 A | 4/1990 | Karpf |
| 4,950,297 A | 8/1990 | Elloy et al. |
| 4,963,153 A | 10/1990 | Noesberger et al. |
| 5,011,496 A | 4/1991 | Forte et al. |
| 5,030,237 A | 7/1991 | Sorbie et al. |
| 5,037,439 A | 8/1991 | Albrektsson et al. |
| 5,047,057 A | 9/1991 | Lawes |
| 5,092,895 A | 3/1992 | Albrektsson et al. |
| 5,108,441 A | 4/1992 | McDowell |
| 5,133,760 A | 7/1992 | Petersen et al. |
| 5,152,797 A | 10/1992 | Luckman et al. |
| 5,314,484 A | 5/1994 | Huene |
| 5,360,450 A | 11/1994 | Giannini |
| 5,370,701 A | 12/1994 | Finn |
| 5,373,621 A | 12/1994 | Ducheyne et al. |
| 5,376,121 A | 12/1994 | Huene et al. |
| 5,395,401 A | 3/1995 | Bahler |
| 5,411,555 A | 5/1995 | Nieder |
| 5,462,563 A | 10/1995 | Shearer et al. |
| 5,507,817 A | 4/1996 | Craig et al. |
| 5,571,196 A | 11/1996 | Stein |
| 5,593,449 A | 1/1997 | Roberson, Jr. |
| 5,702,466 A | 12/1997 | Pappas et al. |
| 5,702,470 A | 12/1997 | Menon |
| 5,702,479 A | 12/1997 | Schawalder |
| 5,702,480 A | 12/1997 | Kropf et al. |
| 5,723,015 A | 3/1998 | Risung et al. |
| 5,725,586 A | 3/1998 | Sommerich |
| 5,782,920 A | 7/1998 | Colleran |
| 5,782,922 A | 7/1998 | Vandewalle |
| 5,782,923 A | 7/1998 | Engelbrecht et al. |
| 5,824,096 A | 10/1998 | Pappas et al. |
| 5,824,103 A | 10/1998 | Williams |
| 5,827,285 A | 10/1998 | Bramlet |
| 5,879,389 A | 3/1999 | Koshino |
| 5,879,395 A | 3/1999 | Tornier et al. |
| 5,944,756 A | 8/1999 | Fischetti et al. |
| 5,957,979 A | 9/1999 | Beckman et al. |
| 5,984,969 A | 11/1999 | Matthews et al. |
| 6,022,352 A | 2/2000 | Vandewalle |
| 6,027,534 A | 2/2000 | Wack et al. |
| 6,039,764 A | 3/2000 | Pottenger et al. |
| 6,051,751 A | 4/2000 | Sioshansi et al. |
| 6,068,658 A | 5/2000 | Insall et al. |
| 6,123,728 A | 9/2000 | Brosnahan et al. |
| 6,139,580 A | 10/2000 | Wurzinger et al. |
| 6,149,687 A | 11/2000 | Gray, Jr. et al. |
| 6,162,253 A | 12/2000 | Conzemius et al. |
| 6,165,221 A | 12/2000 | Schmotzer |
| 6,165,223 A | 12/2000 | Metzger et al. |
| 6,168,630 B1 | 1/2001 | Keller et al. |
| 6,203,575 B1 | 3/2001 | Farey |
| 6,203,576 B1 | 3/2001 | Afriat et al. |
| 6,206,927 B1 | 3/2001 | Fell et al. |
| 6,210,444 B1 | 4/2001 | Webster et al. |
| 6,210,445 B1 | 4/2001 | Zawadzki |
| 6,217,616 B1 | 4/2001 | Ogilvie |
| 6,217,618 B1 | 4/2001 | Hileman |
| 6,264,696 B1 | 7/2001 | Reigner et al. |
| 6,270,529 B1 | 8/2001 | Terrill-Grisoni et al. |
| 6,290,725 B1 | 9/2001 | Weiss et al. |
| 6,306,171 B1 | 10/2001 | Conzemius |
| 6,306,172 B1 | 10/2001 | O'Neil |
| 6,306,174 B1 | 10/2001 | Gie et al. |
| 6,319,283 B1 | 11/2001 | Insall et al. |
| 6,321,606 B1 | 11/2001 | Ishii et al. |
| 6,342,075 B1 | 1/2002 | MacArthur |
| 6,355,037 B1 | 3/2002 | Crosslin et al. |
| 6,358,283 B1 | 3/2002 | Högfors et al. |
| 6,361,563 B2 | 3/2002 | Terrill-Grisoni et al. |
| 6,361,564 B1 | 3/2002 | Marceaux et al. |
| 6,379,387 B1 | 4/2002 | Tornier |
| 6,413,279 B1 | 7/2002 | Metzger et al. |
| 6,428,577 B1 | 8/2002 | Evans et al. |
| 6,436,137 B2 | 8/2002 | Wang et al. |
| 6,443,991 B1 | 9/2002 | Running |
| 6,447,549 B1 | 9/2002 | Taft |
| 6,475,241 B2 | 11/2002 | Pappas |
| 6,494,913 B1 | 12/2002 | Huebner |
| 6,494,914 B2 | 12/2002 | Brown et al. |
| 6,503,280 B2 | 1/2003 | Repicci |
| 6,520,964 B2 | 2/2003 | Tallarida et al. |
| 6,554,838 B2 | 4/2003 | McGovern et al. |
| 6,569,203 B1 | 5/2003 | Keller |

(56) References Cited

U.S. PATENT DOCUMENTS

| | | | |
|---|---|---|---|
| 6,656,225 B2 | 12/2003 | Martin | |
| 6,660,039 B1 | 12/2003 | Evans et al. | |
| 6,699,290 B1 | 3/2004 | Wack et al. | |
| 6,709,459 B1 | 3/2004 | Cooney, III et al. | |
| 6,716,248 B2 | 4/2004 | Huene | |
| 6,726,723 B2 | 4/2004 | Running | |
| 6,767,368 B2 | 7/2004 | Tornier | |
| 6,770,077 B2 | 8/2004 | Van Zile et al. | |
| 6,770,098 B1 | 8/2004 | Hauri et al. | |
| 6,774,155 B2 | 8/2004 | Martakos et al. | |
| 6,797,005 B2 | 9/2004 | Pappas | |
| 6,800,670 B2 | 10/2004 | Shen et al. | |
| 6,818,020 B2 | 11/2004 | Sun et al. | |
| 6,855,165 B2 | 2/2005 | Fell et al. | |
| 6,866,684 B2 | 3/2005 | Fell et al. | |
| 6,890,357 B2 | 5/2005 | Tornier | |
| 6,893,463 B2 | 5/2005 | Fell et al. | |
| 6,911,044 B2 | 6/2005 | Fell et al. | |
| 6,923,831 B2 | 8/2005 | Fell et al. | |
| 6,966,928 B2 | 11/2005 | Fell et al. | |
| 6,972,039 B2 | 12/2005 | Metzger et al. | |
| 6,986,791 B1 | 1/2006 | Metzger | |
| 6,997,957 B2 | 2/2006 | Huene | |
| 7,008,454 B2 | 3/2006 | Fenning et al. | |
| 7,014,660 B2 | 3/2006 | Fenning et al. | |
| 7,105,026 B2 | 9/2006 | Johnson et al. | |
| 7,115,131 B2 | 10/2006 | Engh et al. | |
| 7,150,761 B2 | 12/2006 | Justin et al. | |
| 7,160,329 B2 | 1/2007 | Cooney, III et al. | |
| 7,172,596 B2 | 2/2007 | Coon et al. | |
| 7,189,262 B2 | 3/2007 | Hayes, Jr. et al. | |
| 7,247,170 B2 | 7/2007 | Graham et al. | |
| 7,258,701 B2 | 8/2007 | Aram et al. | |
| 7,297,161 B2 | 11/2007 | Fell | |
| 7,297,164 B2 | 11/2007 | Johnson et al. | |
| 7,338,524 B2 | 3/2008 | Fell et al. | |
| 7,344,540 B2 | 3/2008 | Smucker et al. | |
| 7,384,430 B2 | 6/2008 | Greer et al. | |
| 7,387,644 B2 | 6/2008 | Beynnon et al. | |
| 7,407,513 B2 * | 8/2008 | Alleyne et al. | 623/17.16 |
| 7,419,507 B2 | 9/2008 | Cook et al. | |
| 7,449,028 B2 | 11/2008 | Ball | |
| 7,452,381 B2 | 11/2008 | Steinmann | |
| 7,491,235 B2 | 2/2009 | Fell | |
| 7,513,912 B2 | 4/2009 | Hayes, Jr. et al. | |
| 7,520,901 B2 | 4/2009 | Engh et al. | |
| 7,527,650 B2 | 5/2009 | Johnson et al. | |
| 7,544,209 B2 | 6/2009 | Lotke | |
| 7,608,110 B2 | 10/2009 | O'Driscoll et al. | |
| 7,615,081 B2 | 11/2009 | Justin et al. | |
| 7,641,689 B2 | 1/2010 | Fell et al. | |
| 8,998,994 B2 | 4/2015 | Winslow et al. | |
| 2001/0021876 A1 | 9/2001 | Terrill-Grisoni et al. | |
| 2001/0027345 A1 | 10/2001 | Merrill et al. | |
| 2001/0037154 A1 | 11/2001 | Martin | |
| 2002/0007219 A1 | 1/2002 | Merrill et al. | |
| 2002/0120339 A1 | 8/2002 | Callaway et al. | |
| 2003/0040805 A1 | 2/2003 | Minamikawa | |
| 2003/0208276 A1 | 11/2003 | Berelsman et al. | |
| 2003/0212457 A1 | 11/2003 | Martin | |
| 2003/0225413 A1 | 12/2003 | Sanford et al. | |
| 2004/0186580 A1 | 9/2004 | Steinmann | |
| 2004/0193278 A1 | 9/2004 | Maroney et al. | |
| 2004/0220675 A1 | 11/2004 | Lewis et al. | |
| 2004/0260398 A1 | 12/2004 | Kelman | |
| 2005/0049710 A1 | 3/2005 | O'Driscoll et al. | |
| 2005/0075735 A1 | 4/2005 | Berelsman et al. | |
| 2005/0216090 A1 | 9/2005 | O'Driscoll et al. | |
| 2006/0004462 A1 | 1/2006 | Gupta | |
| 2006/0052725 A1 | 3/2006 | Santilli | |
| 2006/0064173 A1 | 3/2006 | Guederian | |
| 2006/0100712 A1 | 5/2006 | Ball | |
| 2006/0100713 A1 | 5/2006 | Ball | |
| 2006/0100715 A1 * | 5/2006 | De Villiers | 623/23.4 |
| 2006/0111788 A1 | 5/2006 | Ball | |
| 2006/0111789 A1 | 5/2006 | Ball | |
| 2006/0116771 A1 | 6/2006 | Cooney, III et al. | |
| 2006/0142866 A1 | 6/2006 | Baratz et al. | |
| 2006/0173546 A1 | 8/2006 | Berelsman et al. | |
| 2006/0224243 A1 | 10/2006 | Pare et al. | |
| 2006/0282169 A1 | 12/2006 | Felt et al. | |
| 2007/0073408 A1 | 3/2007 | Acker et al. | |
| 2007/0073409 A1 | 3/2007 | Cooney, III et al. | |
| 2008/0154384 A1 | 6/2008 | Acker et al. | |
| 2008/0177393 A1 | 7/2008 | Grant et al. | |
| 2008/0195217 A1 | 8/2008 | Scheker | |
| 2008/0288079 A1 | 11/2008 | Leibel | |
| 2009/0024221 A1 | 1/2009 | Ball | |
| 2009/0036991 A1 | 2/2009 | Steinmann | |
| 2009/0076618 A1 | 3/2009 | Auberger | |
| 2009/0105839 A1 | 4/2009 | Ikegami et al. | |
| 2009/0281631 A1 | 11/2009 | Naidu | |
| 2009/0281632 A1 | 11/2009 | Naidu | |
| 2009/0312839 A1 | 12/2009 | Scheker et al. | |
| 2009/0312840 A1 | 12/2009 | Morrey | |
| 2010/0030339 A1 | 2/2010 | Berelsman et al. | |

FOREIGN PATENT DOCUMENTS

| | | |
|---|---|---|
| DE | 3529894 A1 | 3/1987 |
| DE | 9110504 U1 | 12/1991 |
| DE | 4331282 A1 | 3/1995 |
| EP | 0186471 A2 | 7/1986 |
| EP | 0349173 A1 | 1/1990 |
| EP | 0519873 A2 | 12/1992 |
| EP | 0529408 A1 | 3/1993 |
| EP | 1732476 | 12/2006 |
| FR | 2663536 A1 | 12/1991 |
| FR | 2663838 A1 | 1/1992 |
| FR | 2821545 A1 * | 9/2002 |
| GB | 1520162 A | 8/1978 |
| GB | 2223950 B | 6/1992 |
| GB | 2429164 B | 12/2008 |
| GB | 2507640 A | 5/2014 |
| JP | 2000-342610 A | 12/2000 |
| JP | 2002-524139 A | 8/2002 |
| JP | 4607948 B2 | 1/2011 |
| WO | 9208424 A1 | 5/1992 |
| WO | 0013617 A1 | 3/2000 |
| WO | 2005020851 A2 | 3/2005 |
| WO | 2005086939 A3 | 9/2005 |

OTHER PUBLICATIONS

Swanson Radial Head Implant Product Information, Jan. 29, 2003.
Van Riet et al, The Journal of Bone & Joint Surgery, Capitellar Erosion Caused by a Metal Radial Head Prosthesis. A Case Report, 2004.
Biomet Orthopedics, Inc., Explor Modular Radial Head Surgical Technique, Mar. 2004.
Grewal et al, The Journal of Bone & Joint Surgery, Comminuted Radial Head Fractures Treated with a Modular Metallic Radial Head Arthroplasty. Study of Outcomes, 2006.
Shore et al, The Journal of Bone & Joint Surgery, Chronic Post-traumatic Elbow Disorders Treated with Metallic Radial Head Arthroplasty, 2008.
ACUMED®, Anatomic Radial Head System brochure, Nov. 2008.
Cowcill, Gabrielle, Examiner; U.K. Intellectual Property Office, Patents Act 1977—Combined Search and Examination Report under Sections 17 and 18(3);U.K. Patent Application U.S. Appl. No. GB1316103.9 (counterpart); report date: Mar. 3, 2014.
KMI, Katalyst Bipolar Radial Head System Brochure, no date provided.
Rayhack Osteotomy Systems, Ulnar Shortening Summary, no date provided.
Miss Gabrielle Cowcill, Examiner, UK Intellectual Property Office, "Examination Report Under Section 18(3)" in connection with corresponding UK Application No. GB1316103.9, dated Jan. 8, 2015, 2 pages.

* cited by examiner

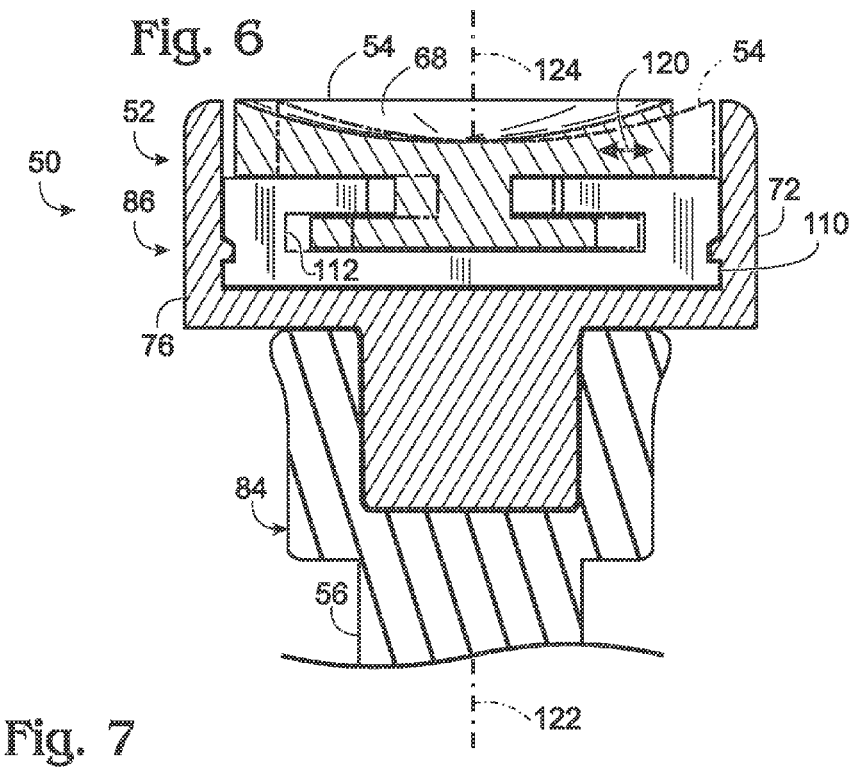
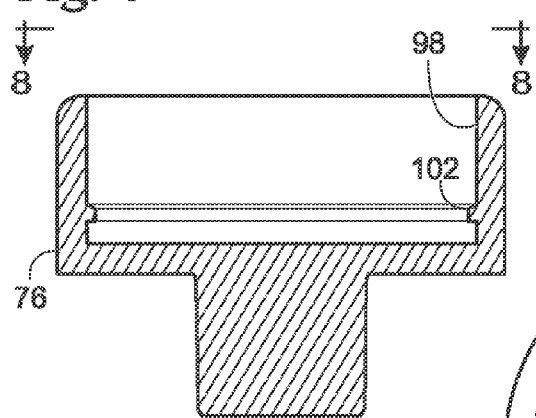
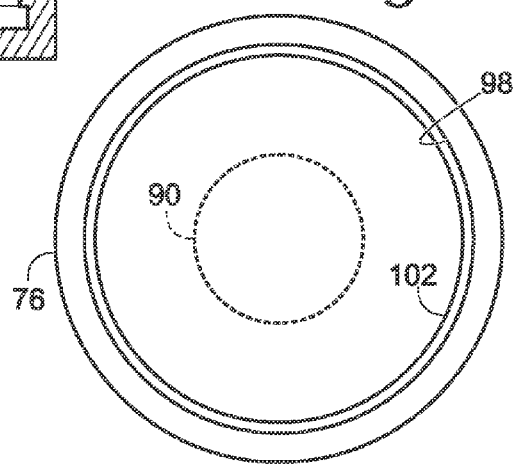

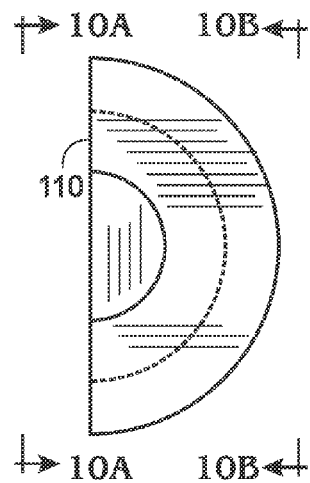
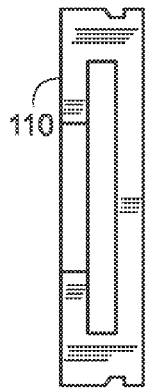
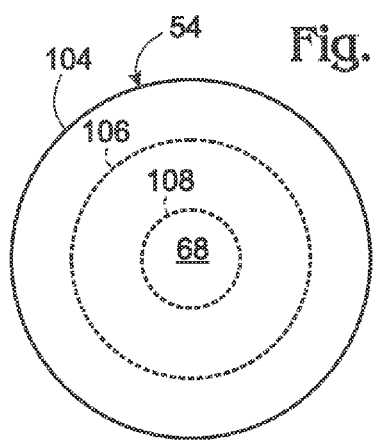
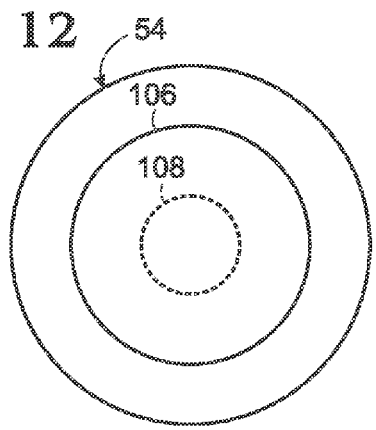

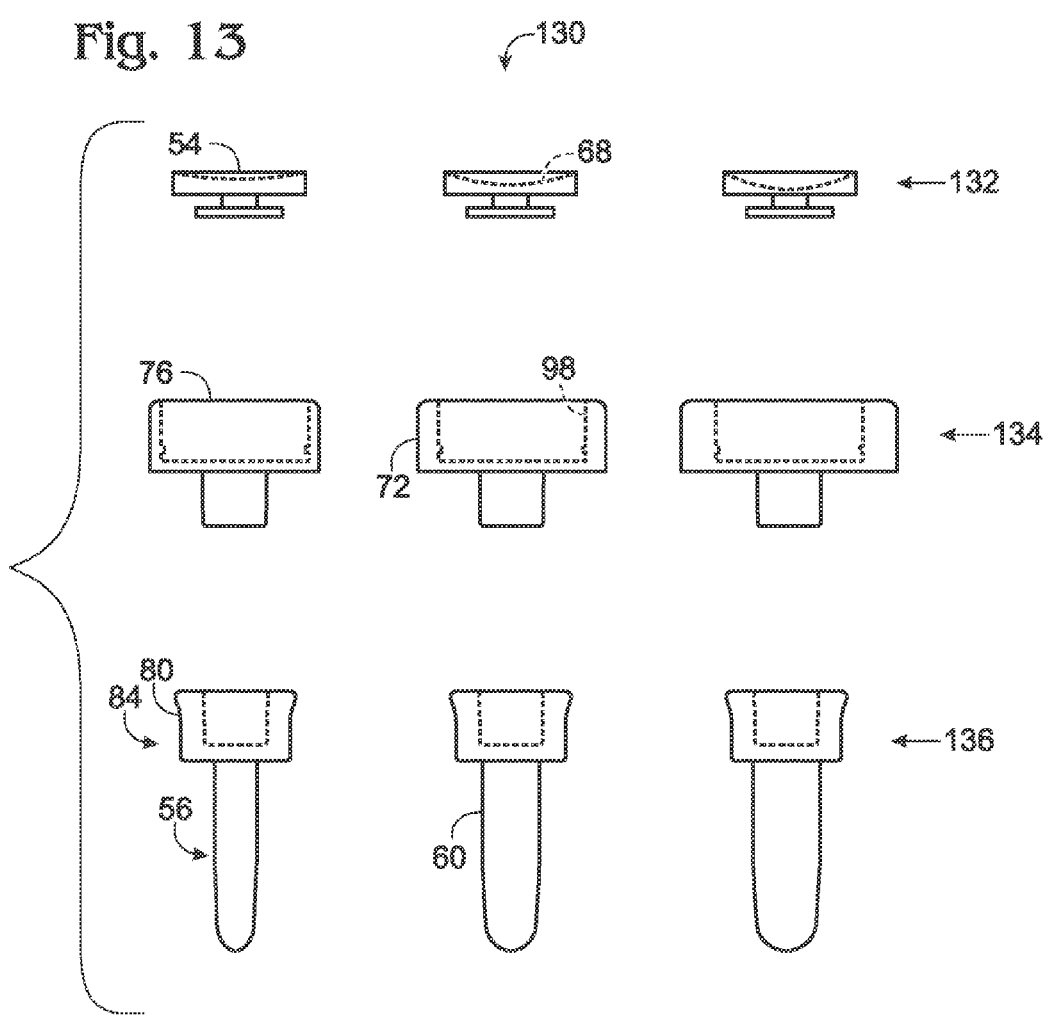

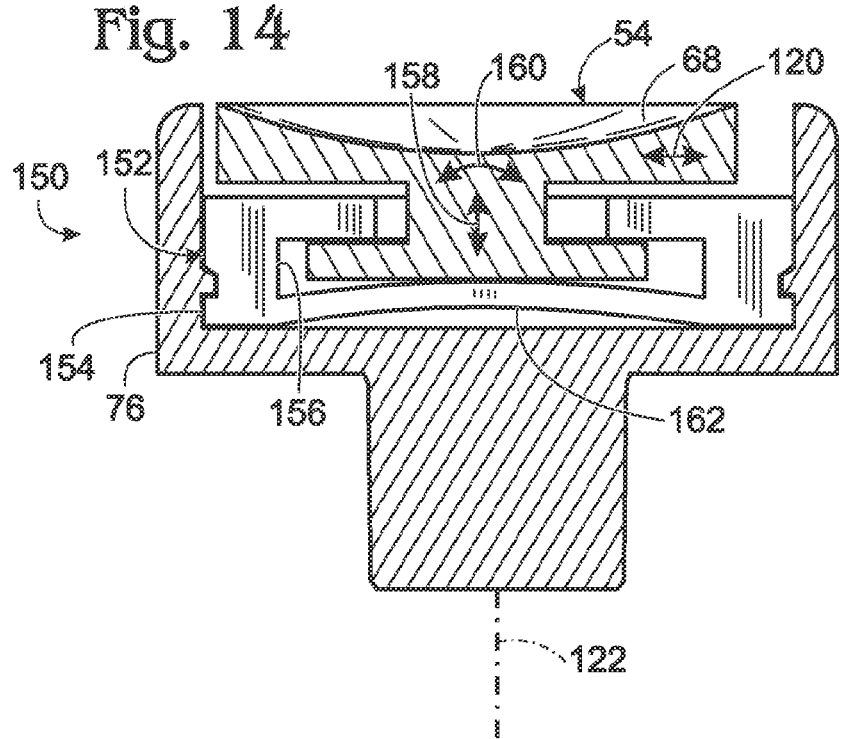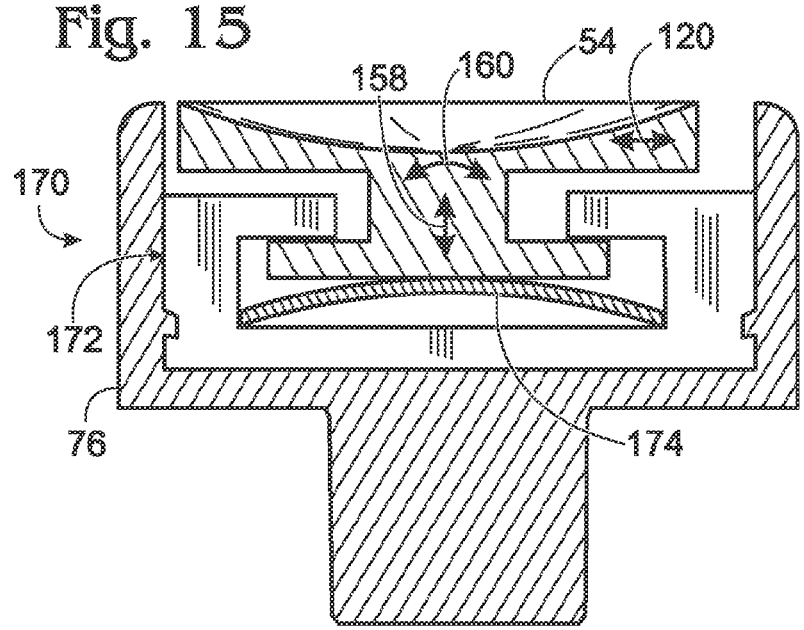

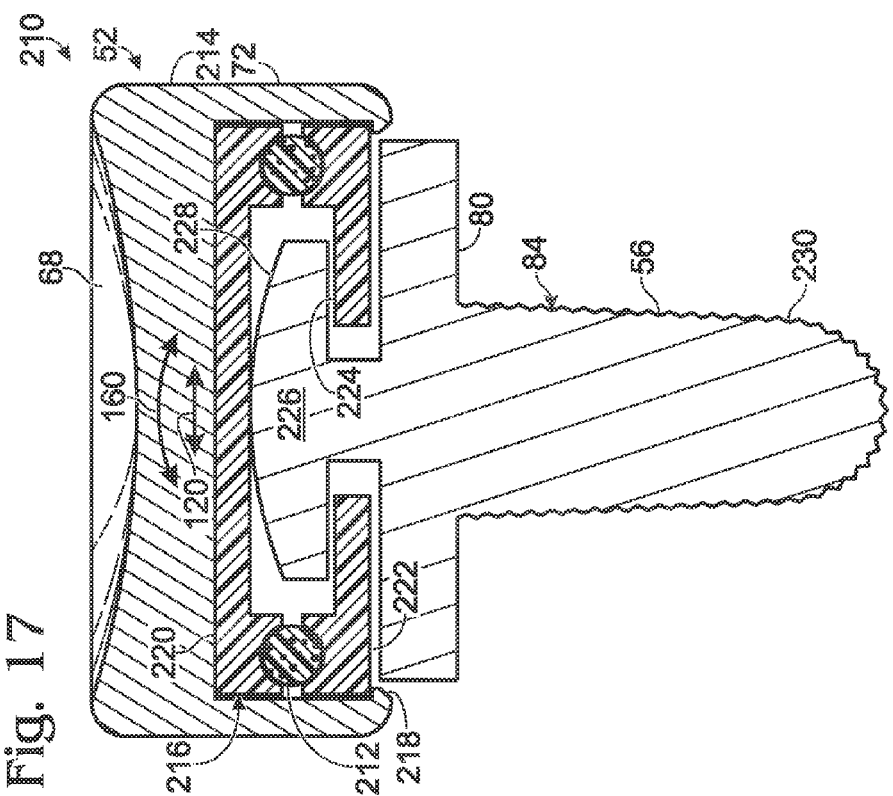
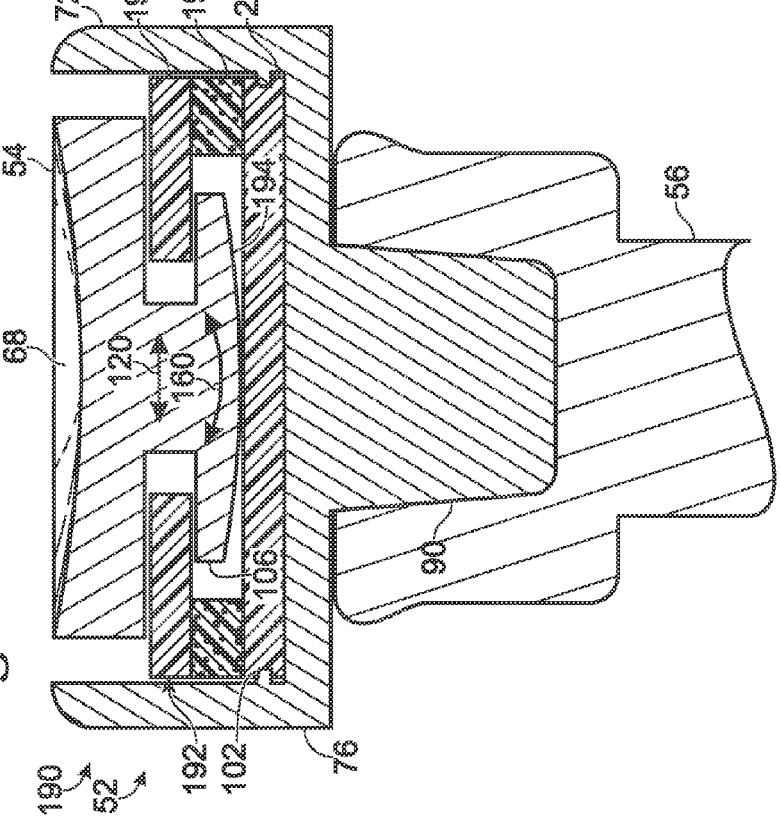

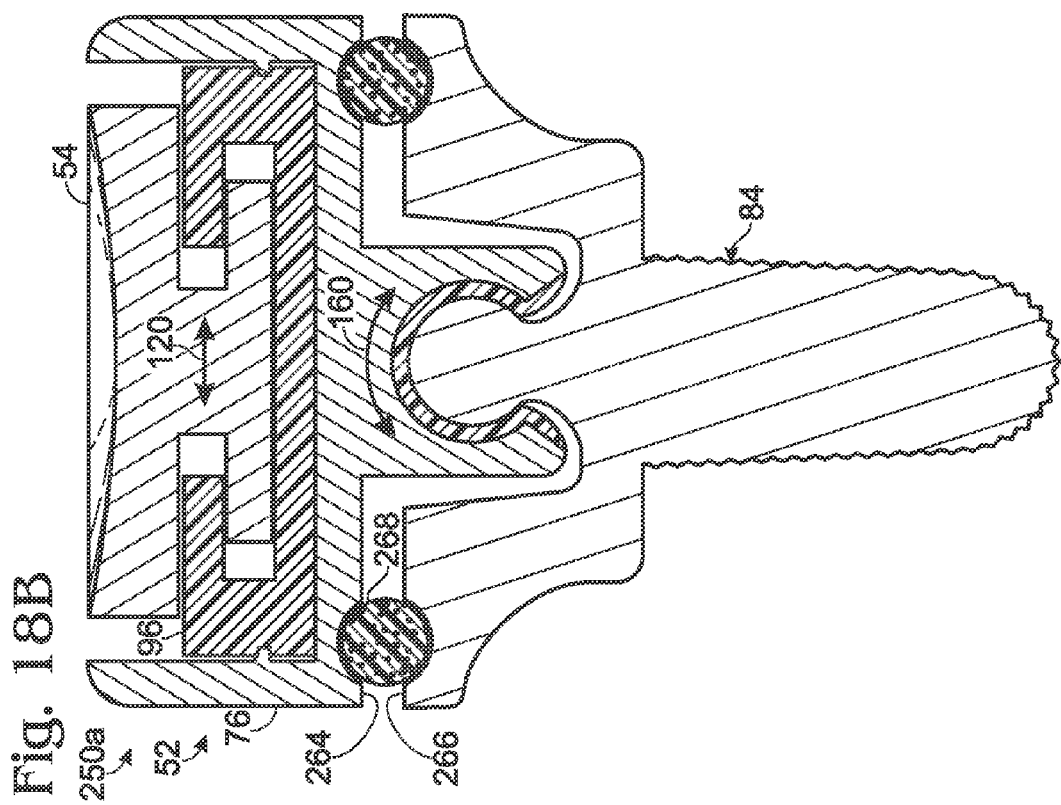
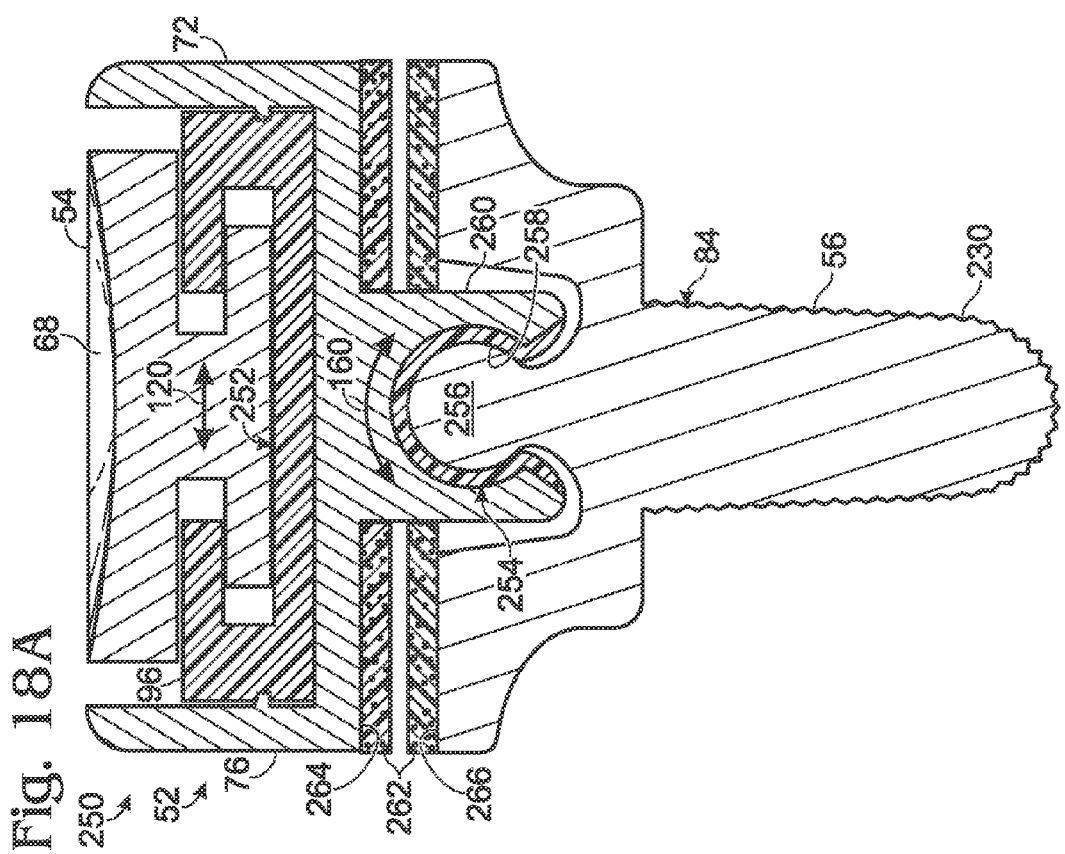

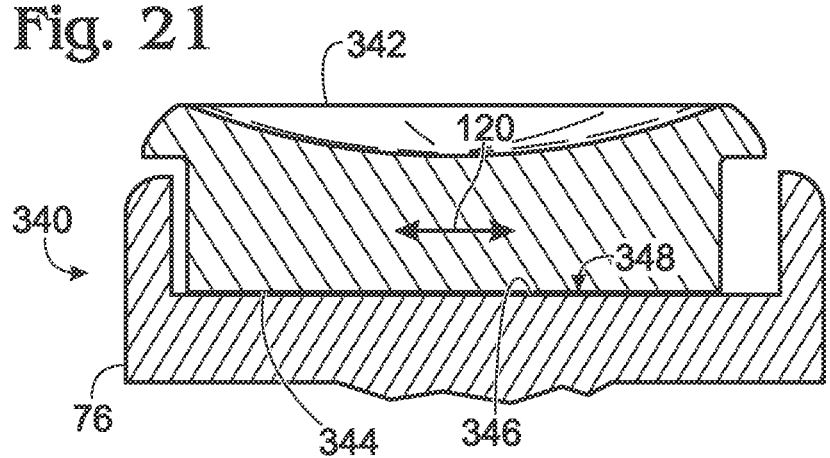
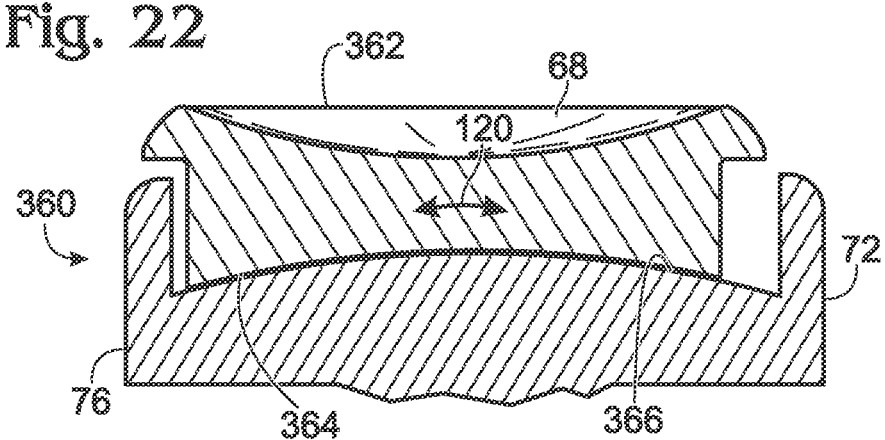

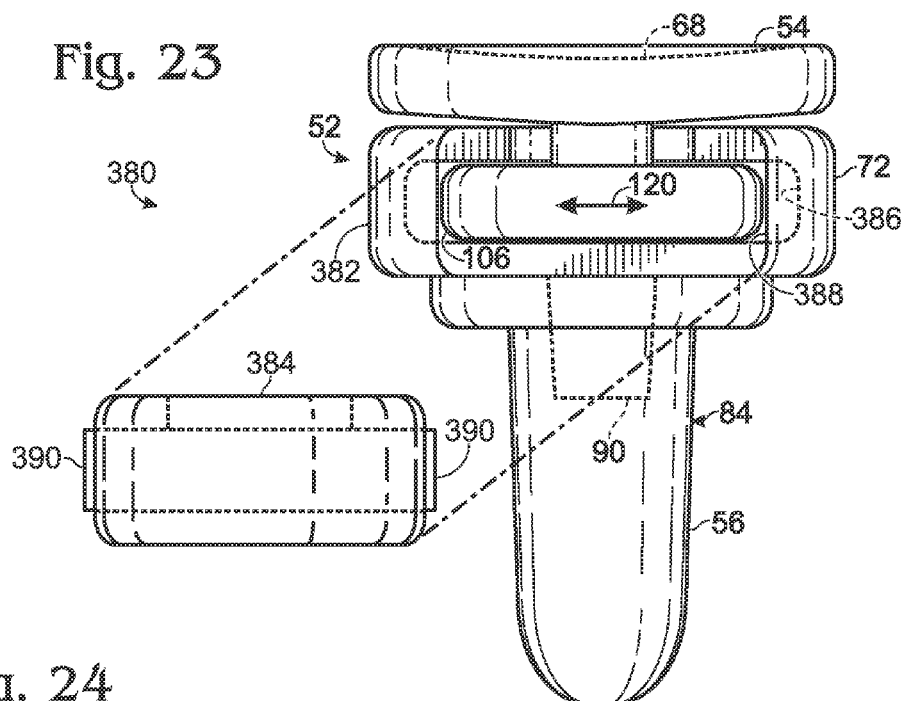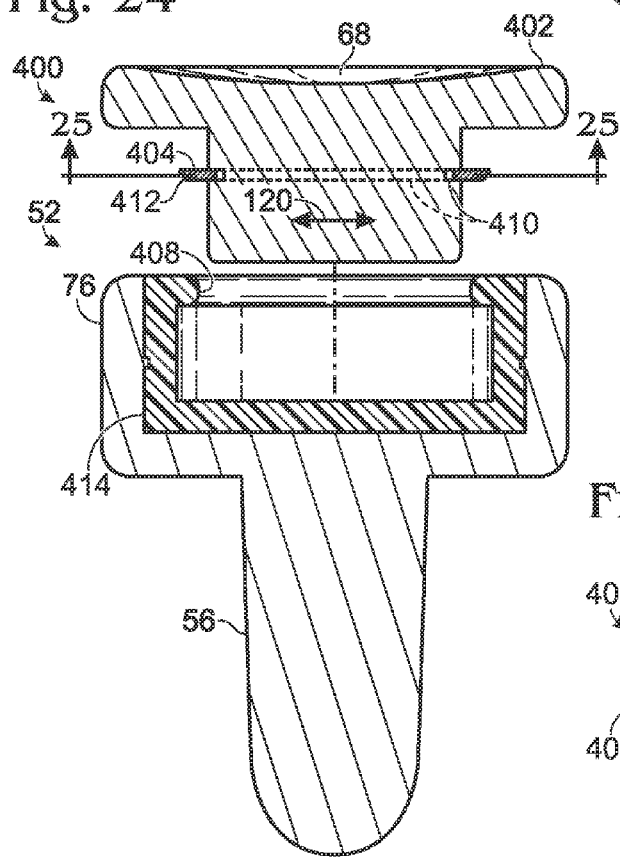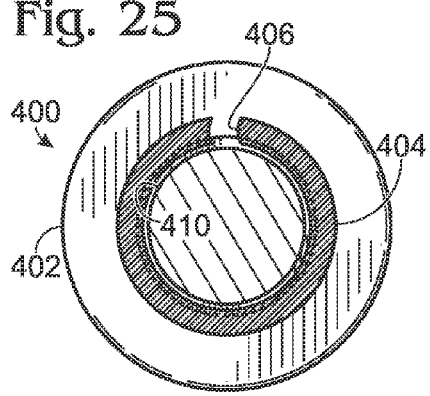

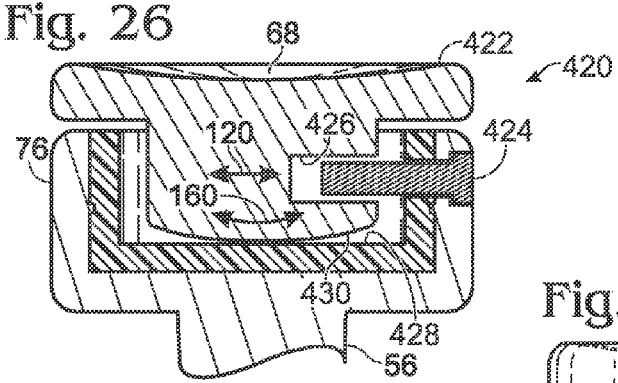
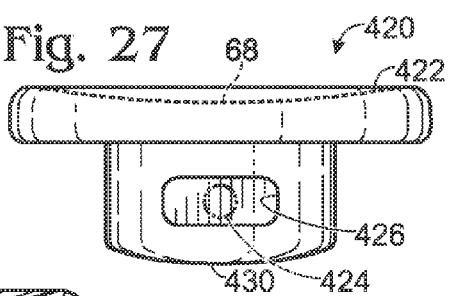
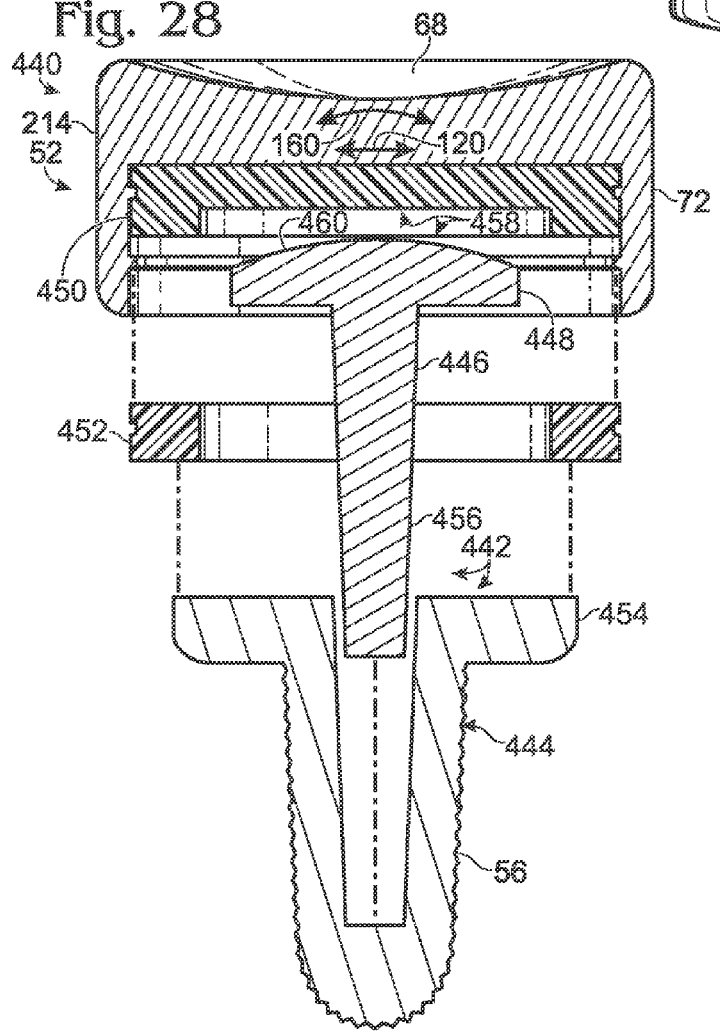

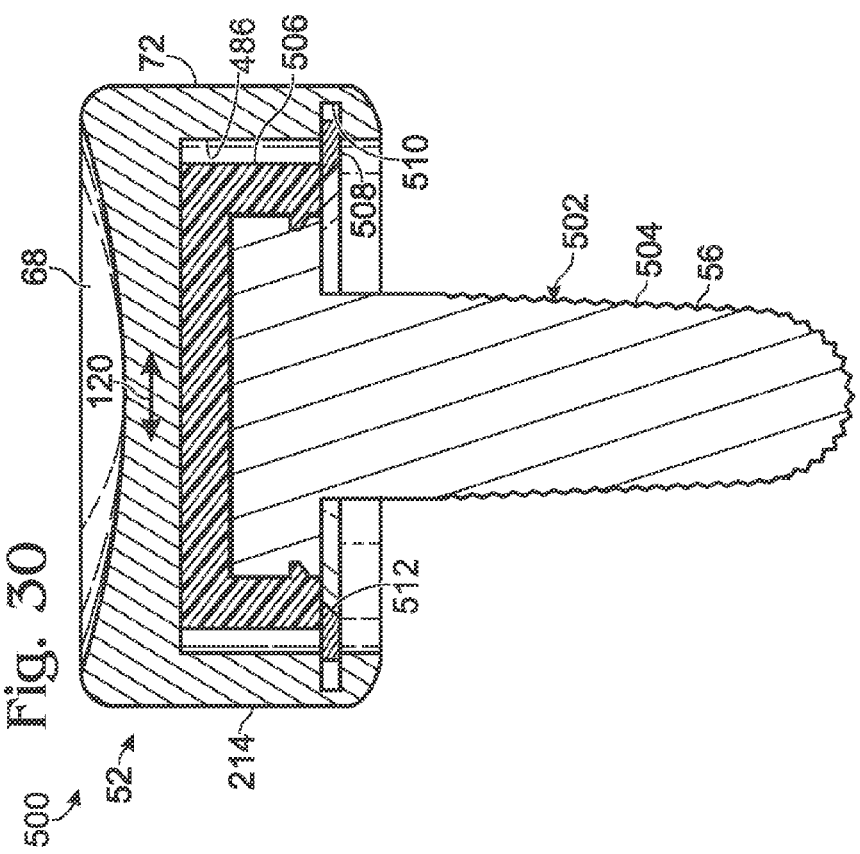
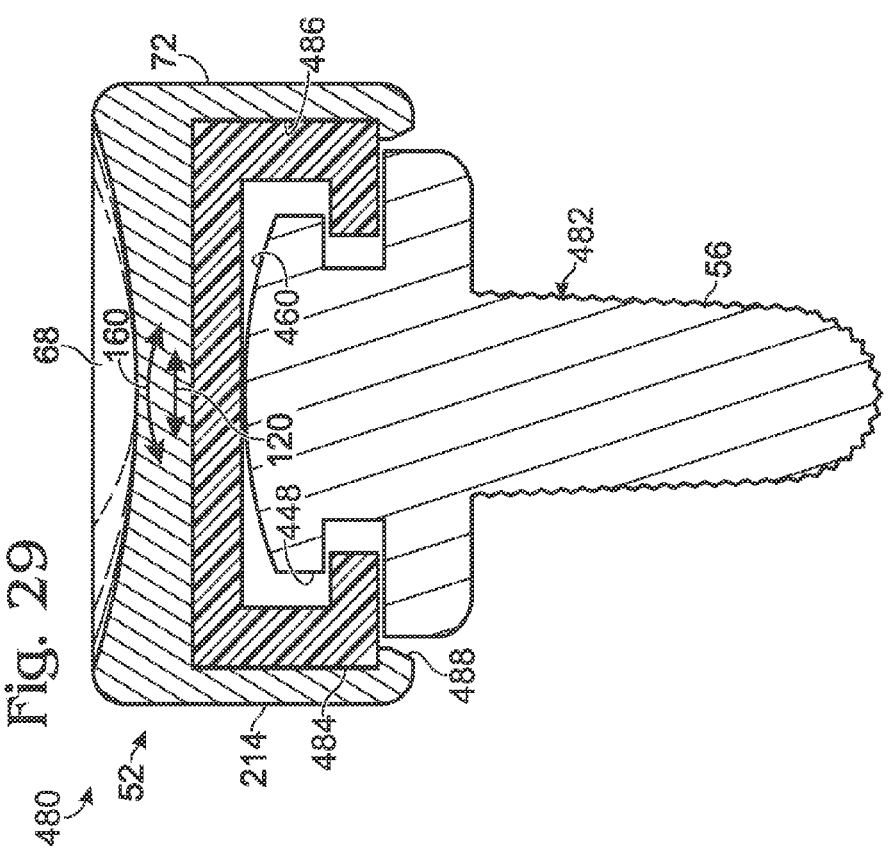

RADIAL HEAD PROSTHESIS WITH FLOATING ARTICULAR MEMBER

CROSS-REFERENCE TO PRIORITY APPLICATION

This application is based upon and claims the benefit under 35 U.S.C. §119(e) of U.S. Provisional Patent Application Ser. No. 61/699,070, filed Sep. 10, 2012, which is incorporated herein by reference in its entirety for all purposes.

INTRODUCTION

The human elbow joint is formed at the junction of the humerus, radius, and ulna. In this compound joint, the proximal head of the radius, or "radial head," articulates at its end with the capitellum of the humerus, to form the humeroradial joint, and on its side with the radial notch of the ulna, to form the proximal radioulnar joint. The radial head thus provides two articular surface regions in the elbow joint: (1) a concave, generally spherical end surface region for articulation with the capitellum, and (2) a convex, roughly cylindrical, side surface region for articulation with the radial notch.

The end and side of the radial head permit the radius to achieve distinct motions when the arm is flexed and extended, relative to when the hand is pronated and supinated. During flexion and extension, the end of the radial head moves on the curved surface of the capitellum, with the humeroradial joint functioning as a hinge joint. In contrast, when the hand is rotated to change its pronation-supination position, the end of the radial head pivots on the capitellum, and the side of the radial head turns in the radial notch.

Trauma to the elbow joint frequently involves damage to the ligamentous support of the elbow and the elbow's osseous structures. The radial head often is fractured either in isolation or in combination with other injuries to the bony or ligamentous structures of the joint; such fractures can be reconstructable or unreconstructable. In general, unreconstructable radial head fractures result from high-energy trauma and therefore frequently are associated with significant injuries to other aspects of the elbow. In such cases, restoration of the stabilizing function of the radial head is crucial to allowing the ligamentous damage and other injuries to heal properly. To achieve this, prosthetic replacement of the entire radial head has become relatively common.

A radial head prosthesis can be fashioned from a single piece of metal, often an alloy including cobalt and chromium ("cobalt-chrome"). Alternatively, to overcome various problems associated with the insertion and removal of such one-piece devices, modular radial head prostheses have been developed that can be assembled during surgery. In any event, the prosthesis generally includes a stem and a head. The stem is received in a medullary cavity of the radius. The head may be shaped to approximate the natural anatomy of the radial head. In particular, the head provides an end surface region and a side surface region, which are artificial replacement surfaces corresponding to the natural articular surfaces described above.

A shortcoming of radial head prostheses in the prior art is the difficulty of accurately positioning both the end and side articular surfaces of the prosthesis for proper articulation with the capitellum and radial notch, respectively.

SUMMARY

The present disclosure provides a system, including apparatus, methods, and kits, for replacement of the proximal end of a radial bone with a prosthesis having a floating articular member. The prosthesis may include a head portion connected or connectable to a stem portion. While the stem portion remains operatively connected to the head portion, the head portion and/or an articular member thereof may be permitted to float in position relative to the stem portion. The head portion/articular member may float transversely (e.g., translationally) and/or rotationally with respect to the stem portion. The articular member may articulate with a humeral bone or both a humeral bone and an ulnar bone. In some embodiments, the head portion may include a fixed member for articulation with an ulnar bone and a floating member for articulation with a humeral bone.

BRIEF DESCRIPTION OF THE DRAWINGS

FIG. 6 is a fragmentary sectional view of the prosthesis of FIG. 1, taken generally along line 6-6 of FIG. 2.

FIG. 7 is a sectional view of the cup member of the prosthesis of FIG. 1, taken generally as in FIG. 6 but in isolation from other prosthesis components.

FIG. 8 is a top view of the cup member of FIG. 7, taken generally along line 8-8 of FIG. 7.

FIG. 9 is a top view of one of the retainer components of the prosthesis of FIG. 1, taken generally along line 9-9 of FIG. 4.

FIG. 10A is inner side view of the retainer component of FIG. 9, taken generally along line 10A-10A of FIG. 9.

FIG. 10B is an outer side view of the retainer component of FIG. 9, taken generally along line 10B-10B of FIG. 9.

FIG. 11 is a top view of the dish member of the prosthesis of FIG. 1.

FIG. 12 is a bottom view of the dish member of the prosthesis of FIG. 1.

FIG. 13 is a view of selected components of an exemplary elbow repair system, in accordance with aspects of the present disclosure.

FIG. 14 is a sectional view of a second embodiment of a radial head prosthesis having a floating dish member for engagement with the capitellum, taken generally as in FIG. 6 but with only the head portion visible and with the dish member having a biased position produced by a biasing member, in accordance with aspects of the present disclosure.

FIG. 15 is a sectional view of a third embodiment of a radial head prosthesis having a floating dish member for engagement with the capitellum, taken generally as in FIG. 6 but with only the head portion visible and with the dish member having a biased position produced by a biasing member, in accor- FIG. 16 is a fragmentary sectional view of a fourth embodiment of a radial head prosthesis having a floating articular member, taken generally as in FIG. 6, with the articular member captured by a retainer that is at least partially resilient, which may provide a shock-absorbing and/or biasing function, in accordance with aspects of the present disclosure.

FIG. 17 is a sectional view of a fifth embodiment of a radial head prosthesis having a floating articular member, with the articular member being an inverted cup member that articulates with the ulna and the humerus, in accordance with aspects of the present disclosure.

FIG. 18A is a sectional view of a sixth embodiment of a radial head prosthesis having a floating articular member forming at least part of the head portion, with the head portion being rotatably connected to a stem portion and with at least one resilient member disposed between the head portion and the stem portion, in accordance with aspects of the present disclosure.

FIG. 18B is a sectional view of a seventh embodiment of a radial head prosthesis having a floating articular member forming at least part of the head portion, with the head portion being rotatably connected to a stem portion as in FIG. 18A and with a resilient ring replacing the resilient members of FIG. 18A, in accordance with aspects of the present disclosure.

FIG. 21 is a fragmentary sectional view of a tenth embodiment of a radial head prosthesis having a floating articular member, with the articular member having a flat bottom surface that is slidably engaged with a flat floor region of a cup member, in accordance with aspects of the present disclosure.

FIG. 22 is a fragmentary sectional view of an eleventh embodiment of a radial head prosthesis having a floating articular member, with the articular member having a curved and concave (e.g., spherical) surface region that is slidably engaged with a complementary floor region of a cup member, in accordance with aspects of the present disclosure.

FIG. 23 is an exploded side view of a twelfth embodiment of a radial head prosthesis having a floating articular member, with a base region of the articular member being received transversely in a hollow body of the head portion, in accordance with aspects of the present disclosure.

FIG. 24 is an exploded sectional view of a thirteenth embodiment of a radial head prosthesis having a floating articular member, with the articular member being retained with a clip in a cup member, in accordance with aspects of the present disclosure.

FIG. 25 is a sectional view of the prosthesis of FIG. 24, taken generally along line 25-25 of FIG. 24 through the floating articular member and clip.

FIG. 26 is a fragmentary sectional view of a fourteenth embodiment of a radial head prosthesis having a floating articular member, with the articular member being retained in a cup member with a pin, in accordance with aspects of the present disclosure.

FIG. 27 is a side view of the articular member of FIG. 26, taken toward a slot that receives a leading end of the pin.

FIG. 28 is an exploded sectional view of a fifteenth embodiment of a radial head prosthesis having a floating articular member, with the articular member being structured as an inverted cup member held on a support member by a snap-in retainer received in the cup member from below the support member, in accordance with aspects of the present disclosure.

FIG. 29 is a fragmentary sectional view of a sixteenth embodiment of a radial head prosthesis having a floating articular member, in accordance with aspects of the present disclosure.

FIG. 30 is a fragmentary sectional view of a seventeenth embodiment of a radial head prosthesis having a floating articular member, with the articular member being structured as an inverted cup member held on a support member by a clip received in a circumferential groove defined by the cup member, in accordance with aspects of the present disclosure.

DETAILED DESCRIPTION

Figure 1:
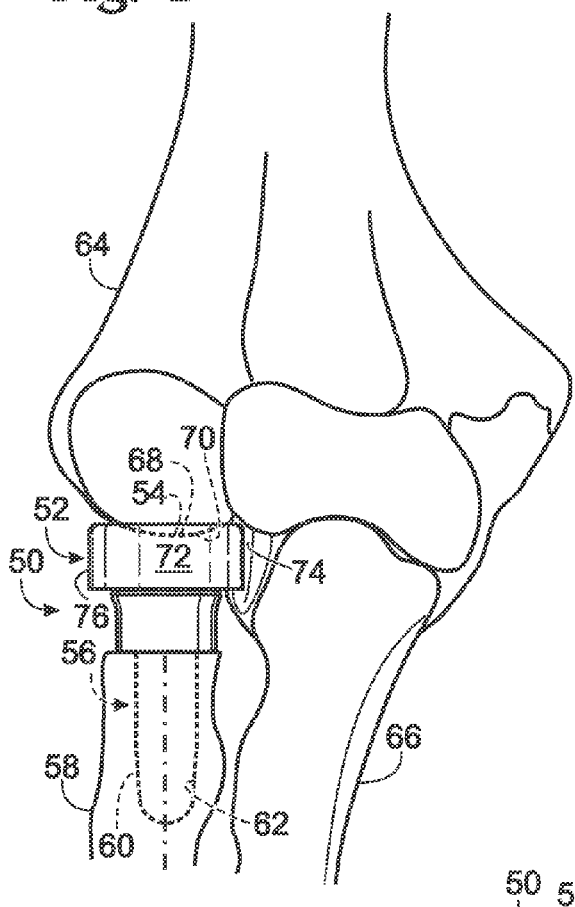
FIG. 1 is an anterior view of a right elbow joint including a first embodiment of an exemplary radial head prosthesis having a head portion that includes a floating, self-centering articular member structured as a dish member for articulation with the capitellum of the humerus, with the prosthesis mounted to the radius such that the head portion replaces the natural radial head, in accordance with aspects of the present disclosure.

The present disclosure provides a system, including apparatus, methods, and kits, for replacement of the proximal end of a radial bone with a prosthesis having a floating articular member. The prosthesis may include a head portion connected or connectable to a stem portion. While the stem portion remains operatively connected to the head portion, the head portion and/or an articular member thereof may be permitted to float in position relative to the stem portion. The head portion/articular member may float transversely (e.g., translationally) and/or rotationally with respect to the stem portion. The articular member may articulate with a humeral bone or both a humeral bone and an ulnar bone. In some embodiments, the head portion may include a fixed member for articulation with an ulnar bone and a floating member for articulation with a humeral bone. In some embodiments, the prosthesis may have at least one resilient member, which may bias a position of the head portion/articular member relative to the stem portion, cushion travel of the head portion/articular member, absorb shocks, and/or the like.

Further aspects of the present disclosure are described in the following sections: (I) exemplary replacement system for a proximal radial head, (II) prosthesis installation, and (III) examples.

I. Exemplary Replacement System for a Proximal Radial Head

This section describes an exemplary replacement system (interchangeably termed an elbow repair system) for a proximal head of a radial bone; see FIGS. 1-13. The system includes an exemplary radial head prosthesis having an articular member that is configured to float (i.e., have a variable position/orientation) during use and with respect to other portions of the prosthesis, which may allow the articular member to be self-centering and/or dynamically/automatically adjustable in position as the radius moves with respect to the adjacent ulna and humerus.

The articular member may be slidable, that is, movable transversely with respect to a long axis of the prosthesis, when the prosthesis is disposed in an operative configuration, namely, when a head portion and a stem portion of the prosthesis are operatively connected to one another. The prosthesis may have a fixed articulation surface region (and/or articular member) for engagement of an ulnar bone (interchangeably termed an ulna) and a movable articulation surface region (and/or articular member) for engagement of a humeral bone (interchangeably termed a humerus). Each surface region and/or articular member that articulates with a bone or bone region forms at least part of a movable joint with that bone or bone region. In other cases, the prosthesis may have a head member that moves as a unit with respect to the stem portion and that articulates with both the ulna and the humerus. In some embodiments, the floating articular member may be capable of sliding transversely and rotating.

The articular member may articulate with a natural region and/or an artificial region of a bone. For example, if the radial head prosthesis is installed in a hemi-arthroplasty procedure that removes the radial head but does not remove the associated radial notch or capitellum, the articular member may articulate with a natural region of an ulnar bone and/or a humeral bone. In other cases, such as when the radial head prosthesis is installed in a total arthroplasty procedure, the articular member of the prosthesis may articulate, at least in part, with an artificial/implanted region (a prosthetic region) of an ulnar bone and/or a humeral bone.

FIG. 1 shows a right elbow joint including an exemplary radial head prosthesis 50 having a head portion 52 that includes a floating articular member, in this case, dish member 54. Prosthesis 50 has a stem portion 56 that mounts the prosthesis and/or head portion 52 to a radial bone 58 (interchangeably termed a radius). In the fully assembled configuration of the prosthesis, before or after prosthesis installation in a recipient, the stem portion is operatively connected to the head portion.

Stem portion 56 may include a shaft 60 disposed in a medullary cavity 62 of the radius. The shaft may be fixed to the radius, such as via an adhesive, one or more fasteners (e.g., bone screws), an interference fit, or a combination thereof, among others.

Head portion 52 is structured and positioned to articulate with (or contact) a humeral bone 64 (interchangeably termed a humerus) and an ulnar bone 66 (interchangeably termed an ulna). More particularly, head portion 52 has a top surface region 68 (interchangeably termed an end or top articular region or contact region) for engagement with capitellum 70 of the humerus and a side surface region 72 (interchangeably termed a side articular region or a side wall) for engagement with radial notch 74 of the ulna. In the depicted embodiment, top surface region 68 is provided by floating dish member 54 and side surface region 72 is provided by a perimeter surface area of a cup member or housing member 76 of head portion 52, with the cup member fixed with respect to stem portion 56. The head portion of prosthesis 50 may be described as a compound head (interchangeably termed a composite head) having two or more discrete components (each formed of one or more discrete pieces) that collectively form the articular surface regions for articulation with the humerus and ulna.

The medial-lateral distance (the M/L offset) from radial notch 74 to the centerline of capitellum 70 is roughly fixed during flexion and extension of the arm. Accordingly, the diameter of head portion 52 (e.g., cup member 76) may be selected according to the M/L offset (generally, by selection of a diameter that is about twice the M/L offset), to roughly center head portion 52 under the capitellum in a medial-lateral direction.

The centerline of capitellum 70 may be offset anteriorly (or posteriorly) from the centerline of radial notch 74, to form an anterior-posterior offset (an A/P offset). Thus, the top articular surface region of head portion 52 may need to be offset correspondingly in an anterior-posterior direction to center the top articular surface region under the capitellum in an anterior-posterior direction. Furthermore, the size of the capitellum varies, so the curvature of the top articular surface region of the head portion may be selected to match the particular curvature of the recipient's capitellum.

Radial head prostheses of the prior art generally provide an implant with a fixed shape and size. Accordingly, to accurately match the anatomy of any given recipient in the operating room, a surgeon needs to have access to a large set of prostheses of different shapes and sizes, to ensure the availability of an implant with a good fit. However, since having a large set of implants is impractical, the surgeon often selects a prosthesis in the operating room from a smaller set of available prostheses and settles for an imperfect fit, which may produce bone wear, such as erosion of the capitellum. The prosthesis thus may function poorly, damage bone, and cause pain.

Improved radial head prostheses are needed that offer more flexibility in selection of a suitable size, shape, and/or position of the replacement head and/or articular surface regions thereof. Prosthesis 50 and other prostheses disclosed herein satisfy the long-felt need for more flexibility in prosthesis selection and positioning. These innovative prostheses may be dynamically positioned and self-centering during flexion-extension and pronation-supination movements of the radial bone.

Figure 2:
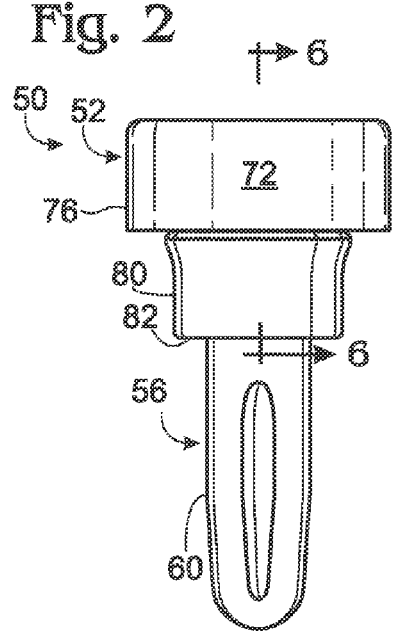
FIG. 2 is a side view of the prosthesis of FIG. 1, taken at elevation in the absence of bone.
Figure 3:
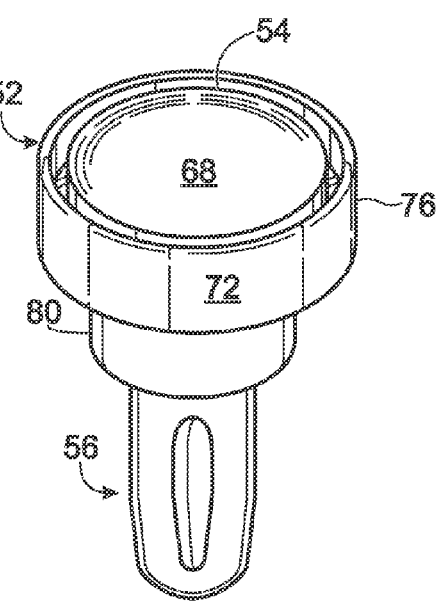
FIG. 3 is another view of the prosthesis of FIG. 1, taken from generally above the prosthesis.

FIGS. 2 and 3 show views of prosthesis 50 in the absence of bone. The prosthesis may include an intermediate portion or collar portion 80 disposed between head portion 52 and stem portion 56. The collar portion may form a shoulder or stop 82 that engages the prepared end of the truncated radius, to stop travel of the stem portion into the radius. The collar portion may have a diameter intermediate the diameter of the head portion and the diameter of the stem portion. The collar portion may be provided by a head component (of one or more discrete pieces) that forms head portion 52, a stem component (of one or more discrete pieces) that forms stem portion 56, by a discrete collar component (of one or more discrete pieces), or any combination thereof. In some cases, the prosthesis may have no collar portion.

Figure 4:
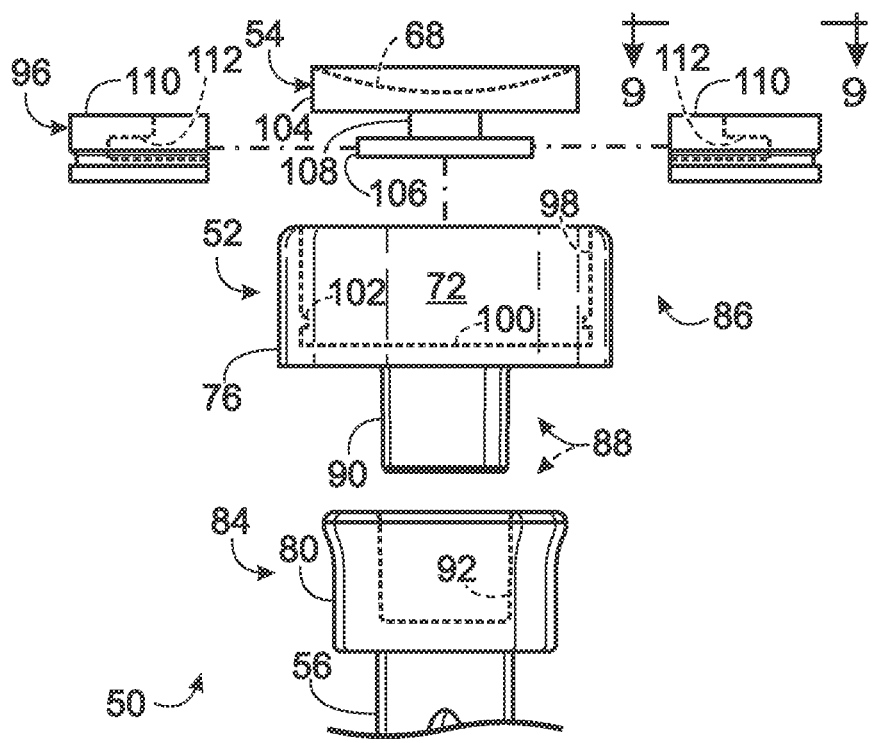
FIG. 4 is a fragmentary, exploded side view of the prosthesis of FIG. 1.

FIG. 4 shows a fragmentary, exploded side view of prosthesis 50. The prosthesis may include a stem component 84 forming stem portion 56 and, optionally, collar portion 80. The stem component may be attached or attachable to a head component 86 at a connection interface 88. The connection interface may, for example, include a projection 90 of head component 86 mated with a complementary recess or socket 92 of the stem component, or vice versa. The connection interface may lock the stem component to the head component. Exemplary connection interfaces may include a tapered recess and a tapered projection (such as a frustoconical taper (e.g., a Morse taper)), a dovetail taper, or the like.

Head component 86 (interchangeably termed a head assembly) may provide all of head portion 52. The head component may include cup member 76, dish member 54, and a retainer 96 that traps the dish member in the cup member. The cup member may be described as a fixed articular member that is fixedly connected to stem portion 56, such that the fixed articular member has a fixed position with respect to the stem portion during movement at the elbow joint (e.g., during movement of the radial bone with respect to the associated ulna and humerus). The dish member may be described as a floating articular member that is movably connected to the stem portion, such that the floating articular member is permitted to have a variable position with respect to the stem portion (and/or the fixed articular member) during movement at the elbow joint (e.g., during movement of the radial bone with respect to the associated ulna and humerus). In some cases, a floating articular member may articulate with both the ulna and the humerus.

Cup member 76 forms side articular surface region 72 for articulation with the radial notch of the ulna. The cup member defines a recess or cavity 98 (e.g., a cylindrical or frustoconical recess, among others) that receives dish member 54 and retainer 96. The recess may have a floor region 100, which may be flat (planar), convex, or concave. In some cases, the floor region may be curved and concave (or convex) (e.g., spherical), for example, corresponding to less than one-half of a sphere, such as less than about 25% or 10% of a complete sphere. A retaining flange 102 (interchangeably termed a detent) may be formed in the cup member around the perimeter of recess 98, such as near the bottom of the recess, as shown, or near or at the top of the recess, among others. (Alternatively, or in addition, at least one detent 102 may be formed by the retainer.) The cup member and/or articular surface region 72 may be formed of metal (e.g., cobalt-chrome) and/or polymer, among others. In some cases, a body of the cup member may be formed of metal, and recess 98 and/or a portion thereof (such as a lower region or the floor region) may be covered with a polymer liner.

Dish member 54 has an upper region 104 that provides top articular surface region 68 for contact with the capitellum. Upper region 104 may be circular (e.g., at least generally disc-shaped) or oval, among others. Top articular surface region 68 may be curved and concave, such as concave spherically. Upper region 104 may be fixed to a base region 106 via a neck region 108. Dish member 54 and/or articular surface region 68 may be formed of metal and/or polymer, among others.

Retainer 96 may be composed of only one component or two or more retainer components 110. For example, in the depicted embodiment, retainer components 110 define openings 112 sized to collectively receive base region 106 and at least part of neck region 108 of dish member 54. The retainer may be formed of metal and/or polymer, among others. In some cases, the cup member and the dish member may be formed of metal, and the retainer may be formed of plastic. More generally, contacting surface regions within the prosthesis that are slidably engaged with one another may be metal against metal, plastic against plastic, or metal against plastic, among others. Furthermore, a pair of such contacting surface regions that movably contact one another both may be flat (planar), one concave and the other convex (e.g., complementary to one another or with different curvatures; see Section III), both convex, or the like.

Figure 5:
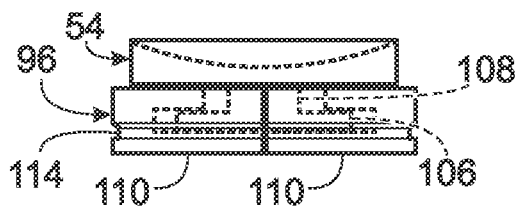
FIG. 5 is a side view of selected components of the prosthesis of FIG. 1, particularly the dish member and a retainer that attaches the dish member to a fixed cup member of the head portion.

FIG. 5 shows a side view of retainer components 110 positioned around base region 106 and neck region 108 of dish member 54. The arrangement of pieces shown in FIG. 5 may be pressed into cup member 76 (see FIG. 4), such that detent 102 of the cup member is received in a groove 114 formed by retainer components 110, to prevent removal of the retainer. The retainer components may be sufficiently resilient to allow the retainer to be snapped into the cup member, to prevent removal of the retainer from the cup member. The retainer may be snapped into a fixed configuration in the cup member, or the retainer may be movably held in the cup member.

FIG. 6 shows a fragmentary sectional view of prosthesis 50 in a fully assembled or operative configuration in which head portion 52 is operatively connected to stem portion 56. Dish member 54 may be capable of transverse motion, indicated at 120, in directions transverse to a long axis 122 defined by stem portion 56 and/or prosthesis 50. Here, dish member 54 is slidable in a plane that is transverse (e.g., orthogonal) to long axis 122, as indicated by a copy of the dish member shown in phantom outline. More particularly, openings 112 of retainer components 110 form a retainer cavity that permits transverse motion (interchangeably termed lateral motion) of base region 106 and neck region 108 (see FIGS. 4 and 5), while preventing removal of the base region from the cavity. As described in more detail below in Section III, the dish member (and/or an articular member and/or the head portion) also may capable of rotating about a fixed or variable transverse axis (e.g., to change the tilt of the dish member/articular member/head portion), pivotal motion about long axis 122 and/or about a head axis 124 that is at least generally parallel to long axis 122, and/or motion (e.g., translational motion) along long axis 122 and/or head axis 124.

Dish member 54 may or may not project above the top of cup member 76. Accordingly, the top of dish member 54 may be approximately flush with the top of cup member 76, or may end below or extend above the top of the cup member by any suitable distance.

FIGS. 7-12 present additional features of prosthesis 50. FIGS. 7 and 8 show respective sectional and top views of cup member 76. Detent 102 may extend partially or completely around recess 98. FIGS. 9, 10A, and 10B show various views of one of retainer components 110. FIGS. 11 and 12 show respective top and bottom views of dish member 54.

FIG. 13 shows selected components of an exemplary elbow repair system 130 for replacement of a natural radial head with a prosthetic head. The system, which may be supplied as a kit, may include at least one dish member 54 or a set 132 of two or more dish members 54, at least one cup member 76 or a set 134 of two or more cup members 76, and at least one stem component 84 and/or stem portion 56 or a set of two or more stem components 84 and/or stem portions 56. The system also may include a retainer to connect a dish member to a cup member, one or more trial implants, instruments to prepare a radial bone, and the like.

Set 132 may be composed of floating articular members or dish members 54 with different top articular surface regions 68. The surface regions 68 may have different curvatures relative to one another, as shown. For example, surface regions 68 may be characterized by different radii of curvature. Alternatively, or in addition, articular surface regions 68 may have distinct diameters, as measured between opposite borders of each surface region, and/or distinct perimeter shapes (e.g., circular and oval, among others).

Set 134 may be composed of fixed articular members 76 (interchangeably termed side articular members or body members (e.g., cup members)) with different side articular surface regions 72. The fixed articular members and/or surface regions 72 may have different outer diameters relative to one another, as shown. Alternatively, or in addition, the fixed articular members may have distinct shapes (e.g., circular and oval, among others), different heights, or the like. Recess 98 may (or may not) have the same size and shape in each fixed articular member.

Set 136 may be composed of stem components and/or stem portions 56 having different shafts 60. For example, the shafts may differ in diameter (as shown), length, cross-sectional shape, or any combination thereof, among others. Collar portion 80, if present, also or alternatively may differ among members of set 136, for example, differing in diameter or height, among others.

An operative prosthesis 50 (e.g., see FIGS. 1, 2, and 6) may be assembled from any suitable combination of a dish member 54 from set 132, a cup member 76 from set 134, and a stem component 84 or stem portion 56 from set 136. A component from each set may be selected that gives a preferred fit (e.g., the best expected fit or measured fit) for a recipient of the prosthesis. Selection of each component may be performed before or during a surgical procedure on the recipient.

A prosthesis with a compound head having a side articular member and an end/top articular member may offer substantial advantages. For example, the compound head may provide substantial advantages over a one-piece prosthetic head, such as offering a surgeon the ability to independently select the size/shape of the top and side articular surface regions of the prosthesis. As a result, the articular surface regions of the installed prosthesis may better approximate the natural (removed) radial head and may complement articular surfaces of adjacent bones more accurately, thereby improving joint function and reducing wear. Also, the top/end articular surface region of the prosthesis may float during use. For example, the top/end articular surface region may be dynamically centered on the capitellum and/or dynamically angled with respect to the long axis of the stem portion of the prosthesis during movement of the radial bone at the elbow joint.

Further aspects of radial head prostheses having a floating articular member are described elsewhere in the present disclosure (e.g., see Section III). In some cases, the prosthesis may have a single floating articular member for contact with both the ulna and the humerus (see Examples 3 and 9). The articular member may provide a pair of articular surface regions for respective engagement with the ulna and the humerus, with the pair of articular surface regions being fixed relative to one another (e.g., with both surface regions being formed by the same continuous surface of the articular member). In some cases, the pair of articular surface regions may be movable relative to one another (e.g., slidable transversely and/or rotatable (e.g., tiltable)).

II. Prosthesis Installation

This section describes exemplary methods of installing a radial head prosthesis having any suitable combination of the features, aspects, and components of the present disclosure. The methods also or alternatively may be described as methods of repairing an elbow joint. In any event, the method steps of this section and elsewhere in the present disclosure may be performed in any suitable order and in any suitable combination.

An elbow joint and/or radial bone may be selected. The elbow joint and/or radial bone may have a damaged (e.g., injured) or missing radial head.

The radial bone may be prepared to receive a radial head prosthesis. The natural radial head may be removed, if present. For example, the radial bone may be cut to remove the radial head. A medullary cavity of the radial bone may be prepared to receive the stem portion of a prosthesis. For example, the cavity may be reamed and/or broached, among others. The cavity may be sized according to the diameter and/or length of a stem portion to be received in the cavity.

A prosthesis for installation may be selected. Selection of the prosthesis may include selecting suitable stem and head components of the prosthesis based on one or more characteristics of the particular elbow joint and/or radial bone to be repaired. For example, a stem component or stem portion may be selected according to the size of the medullary cavity or radial bone, the length of radial bone removed, or the like. Alternatively, or in addition, a side articular member of the head portion, or the entire head portion, may be selected based on the medial-lateral offset of the capitellum relative to the radial notch in the recipient. Furthermore, a floating articular member or dish member may be selected based on a characteristic of the capitellum in the recipient, such as the size, shape, and/or position of the capitellum. Selection of each component may be based on at least one measurement of the elbow joint and/or radius. The measurement may result from a measuring device, such as calipers, a radiographic scale, temporary installation of a trial prosthesis or trial component thereof, or the like. In some cases, aspects of the radial prosthesis may be selected based on one or more characteristics of another prosthesis (e.g., an ulnar prosthesis and/or a humeral prosthesis) to be contacted by the radial prosthesis.

The stem portion of the prosthesis may be inserted into the medullary cavity of the radial bone. The stem portion may be fixed to the radius with the stem portion in the medullary cavity. Fixing the stem portion may be achieved by the act of insertion or may be effected or augmented after insertion of the stem portion (e.g., with fasteners).

The head portion of the prosthesis may be placed in operative attachment (interchangeably termed operative connection) to the stem portion. The head portion, or one or more articular members thereof, may be operatively connected to the stem portion before or after the stem portion is inserted into the medullary cavity.

The head portion of the prosthesis may be assembled. For example, a top articular member of the prosthesis may be operatively connected to a side articular member. This assembly may be performed before or after the side articular member and/or the head portion is operatively connected to the stem portion.

Assembly of the prosthesis may be performed during manufacture or intraoperatively. In some cases, intraoperative assembly may be preferable, to permit a surgeon to select suitable components in the operating room according to the specific anatomy of the recipient. In some embodiments, intraoperative assembly may include connection of a retainer, to establish a predefined range of motion for a head member and/or articular member.

III. Examples

The following examples describe selected aspects and embodiments of the present disclosure including exemplary radial head prostheses (interchangeably termed implants) and methods of installing the prostheses. The components, aspects, and features of the implants described in each of these examples may be combined with one another and with the implants described above, in any suitable combination. These examples are intended for illustration and should not limit the entire scope of the present disclosure.

Example 1

Prosthesis with a Biased Dish Member

This example describes exemplary prostheses having a floating articular member with a position biased, along and/or about at least one axis, by at least one biasing member (e.g., at least one elastic member, such as a spring); see FIGS. 14 and 15.

FIG. 14 shows another embodiment 150 of a prosthesis having a floating dish member 54 for engagement with the capitellum. Prosthesis 150 may be structured generally as described above for prosthesis 50 (see Section I), except that dish member 54 has additional degrees of freedom and has a biased position with respect to cup member 76 and/or along long axis 122.

A modified retainer 152 may determine the range of motion and the biased position of dish member 54 (compare with retainer 96; see FIGS. 4-6, 9, 10A, and 10B). Each retainer component 154 of retainer 152 may define an opening 156, which is larger than the opening of retainer 96. Opening 156 provides clearance for vertical movement of dish member 54, as indicated by a double-headed arrow at 158, along long axis 122 (and/or along the head axis; see FIG. 6). Accordingly, dish member 54 can move translationally parallel to long axis 122. Also, the retainer provides sufficient clearance for the dish member to rotate about a fixed or variable axis transverse to long axis 122, as indicated by a double-headed rotation arrow at 160, to change the orientation (the tilt) of the dish member. The ability of dish member 54 to tilt with respect to the stem portion may allow dish member 54 to achieve a closer static and/or dynamic fit to the capitellum. The dish member and/or the head portion, here and elsewhere in the present disclosure, may be capable of rotating (tilting) any suitable angle from a neutral (e.g., untilted) position, such as at least about 3, 5, 7, 10, or 20 degrees, and/or less than about 40, 30, 20, 15, or 10 degrees, among others.

Retainer 152 also may provide at least one biasing member 162, which here and elsewhere in the present disclosure may be flexible, and may be described as a resilient member, an elastic member, and/or a spring member. Biasing member 162 may bias the position of dish member 54, such as along axis 122. For example, the biasing member may urge the dish member upward, away from the stem portion of the prosthesis, and towards the capitellum. The biasing member may function as a shock absorber and/or may encourage a more constant and uniform engagement of the capitellum as the radius travels through its range of motion with respect to the other bones of the elbow joint. Here, the biasing member is structured as a leaf spring. In other cases, the biasing member may be a coil spring, a resilient pad, a fluid-filled bladder, or the like. However, any suitable biasing mechanism may be incorporated into the head portion of the prosthesis to resiliently position dish member 54 (and/or the head portion) along and/or about any suitable axis or axes. The biasing mechanism may store mechanical energy and supply a restoring force that urges dish member 54 (and/or the head portion) toward an equilibrium or resting position.

FIG. 15 shows another embodiment 170 of a prosthesis having a floating dish member 54 for engagement with the capitellum. Prosthesis 170 may be structured generally as described above for prosthesis 150 (see FIG. 14), with dish member 54 being capable of axial (e.g., vertical) motion and transverse (e.g., horizontal) motion, and having a biased position with respect to cup member 76 and/or along the long axis of the prosthesis. Prosthesis 170 has a retainer 172 containing a biasing member 174 (e.g., a leaf spring) that is a discrete component relative to the retainer and dish member 54. Biasing member 174 may be disposed between surface regions of dish member 54 and retainer 172, with the biasing member inside (as shown here) or outside the opening(s) defined by the retainer. In some embodiments, the biasing member may be integral to dish member 54 (e.g., formed by a resilient base region of the dish member). In some embodiments, the biasing member may be disposed under the retainer, namely, between the retainer and the floor of cup member 76. With this arrangement, the retainer may be capable of moving axially (e.g., vertically) within the cup member, through a predefined range of vertical motion.

Example 2

Prosthesis with Resilient Retainer

This example describes an exemplary prosthesis 190 having a resilient retainer 192 that captures a floating dish member 54 in a cup member 76; see FIG. 16.

Prosthesis 190 may be structured generally as described above for prostheses 50, 150, and 170 (see Section I and Example 1). For example, dish member 54 may be capable of sliding transversely in cup member 76, indicated at 120, to dynamically center the dish member on the capitellum. However, the dish member may have a curved and convex (e.g., spherical) bottom surface region 194 that allows the dish member to rotate (e.g., by rocking), indicated by a double-headed arrow at 160, about a fixed or variable transverse axis, to a tilted configuration that changes the angle defined between the dish member and the long axis of stem portion 56.

Dish member 54 may be held in cup member 76 by retainer 192 that functions generally like retainer 96 (see FIG. 4), except that retainer 192 provides more clearance for vertical movement of the dish member and is least partially elastic. For example, retainer 192 may have an elastic ring portion 196 sandwiched between and affixed to retainer members 198, 200 that are less elastic. The elastic region of retainer 192 may provide a biasing mechanism that biases the position of dish member 54 along a vertical axis, biases the rotational (tilted) position of the dish member, and/or that acts as an elastic bumper that can be contacted by a base region 106 of the dish member to cushion and/or limit lateral motion 120 of the dish member.

Example 3

Prosthesis with Shock Absorption

This example describes an exemplary prosthesis 210 having a resilient, shock-absorbing member 212 disposed within a head portion 52; see FIG. 17.

The head portion may include a single articular member 214 (which interchangeably may be described as a head member or an inverted cup member) that forms top articular surface region 68 and side articular surface region 72 for respective articulation with the humerus and the ulna. Head member 214 may be configured to float with respect to a stem component 84 that provides stem portion 56 and shoulder 80. More particularly, head member 214 and/or head portion 52, as a unit, may be capable of transverse motion 120 and rotational motion 160, with respect to stem portion 56.

Head member 214 may house a retainer assembly 216 that is held within the head member by at least one detent 218. The retainer assembly may include shock-absorbing member 212, which may be structured as an O-ring sandwiched between upper and lower members 220, 222 of retainer assembly 216. Upper and lower members 220, 222 may be spaced from one another, as shown, to permit deformation of shock-absorbing member 212. The shock-absorbing member may deform in response to a vertical load on the head portion (parallel to the long axis of the stem portion), a moment applied to the head portion (e.g., urging the head to tilt), or the like.

Retainer assembly 216 may define a cavity 224 sized and shaped to receive and trap a top protrusion 226 of stem component 84. The top protrusion may have a convex and curved (e.g., spherical) surface region 228 that contacts the ceiling of cavity 224 to facilitate rotational motion 160 (e.g., with surface region 228 rolling along the ceiling of the cavity).

Stem portion 56 may have a rough surface 230, such as titanium plasma coat, to facilitate bony ongrowth that anchors the stem portion more stably in the radial bone.

Example 4

Prostheses with Distinct Joints for Transverse and Rotational Motion

Figure 19:
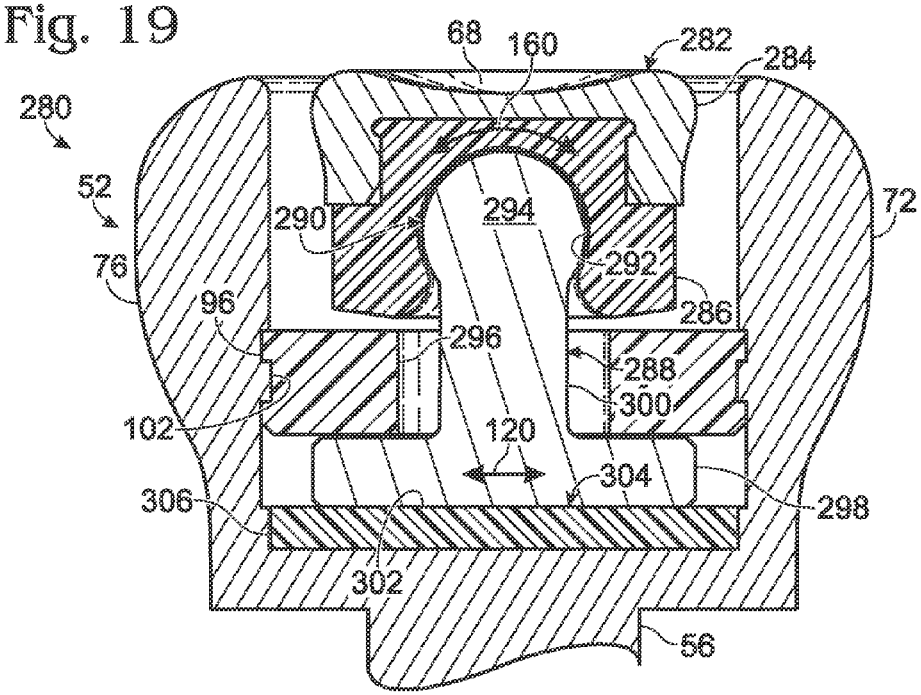
FIG. 19 is a fragmentary sectional view of an eighth embodiment of a radial head prosthesis having a floating articular member forming at least part of the head portion, with the floating articular member including a pivotable joint that allows rotational motion of an upper region of the articular member, in accordance with aspects of the present disclosure.

This example describes exemplary prostheses each having a first joint that permits transverse motion 120 of an articular member and a second joint that permits rotational motion 160 of the articular member; see FIGS. 18A, 18B, and 19.

FIGS. 18A and 18B show prostheses 250 and 250*a* that each permit dish member 54 to undergo transverse motion 120 and pivotal motion 160 via distinct joints. Dish member 54 is capable of transverse motion 120, in this case, translational motion, via sliding at a planar joint 252, as described above (e.g., see Section I). Dish member 54 also is capable of rotational motion, in this case pivotal motion, via a spherical joint 254. Joint 254 may be formed by a ball member 256 defined by stem component 84 and a polymer-lined socket 258 defined by a protruding base region 260 of cup member 76, or vice versa, among others. Pivotal motion at joint 254 allows the entire head portion (including cup member 76 and dish member 54) to be rotated (e.g., tilted) relative to the stem portion.

Prostheses 250 and 250*a* may have different resilient members. Prosthesis 250 (FIG. 18A) may have one or more resilient sheets 262 (e.g., pads or annular sheets) disposed between facing surface regions 264, 266 of the head portion/cup member 52/76 and stem component 84, respectively. The sheet(s) may cushion contact between the head portion and the stem component when the head portion is tilted close to its rotational limit. Prosthesis 250*a* (FIG. 18B) may have a resilient ring 268 disposed between head portion 52 and stem component 84. Ring 268 may (or may not) be in contact with surface regions 264, 266 of both the head portion and the stem component when the head portion is in a neutral position (as shown) and may deform as the head portion is tilted with respect to the stem portion, to cushion tilting motion and/or to bias the rotational position of the head portion, among others.

FIG. 19 shows a radial head prosthesis 280 having a floating articular member 282 for articulation with the capitellum. Floating articular member 282 defines a concave surface region 68 for contacting the capitellum. Articular member 282 may be movable with respect to a fixed articular member 76 (a cup member) that provides an outer side wall 72 for articulation with the ulna. Articular member 76 may be fixed with respect to stem portion 56, and may be formed as one piece with the stem portion, as shown here, or may be fixedly connectable to the stem portion by attaching discrete components to each other (e.g., see Section I).

Floating articular member 282 may be one piece or two or more pieces. For example, in the depicted embodiment, articular member 282 is composed of an upper element 284, which may be formed of metal, and a lower element 286, which may be formed of polymer. Elements 284 and 286 may be fixed to one another such that the elements move together as a unit. Upper element 284 contacts the capitellum, and the lower element 286 supports the upper element.

Articular member 282 may be pivotably connected to and supported by a support member 288 (interchangeably termed a post member), which may be formed of metal. Articular member 282 and support member 288 collectively may form a pivotable joint 290 that permits rotational motion 160 of articular member 282 with respect to stationary regions of the prosthesis (e.g., cup member 76 and stem portion 56). The pivotable joint may, for example, be a ball-and-socket joint. In the depicted embodiment, lower element 286 of articular member 282 defines a socket 292 and support member 288 defines a ball member 294 that is received and trapped in the socket. In other embodiments, the positions of the socket and ball member may be reversed.

Support member 288 may be held in cup member 76 by a retainer 96 engaged with a detent 102 formed by the cup member. Retainer 96 may define an aperture 296 sized to receive a portion of the support member. More particularly, support member 288 may have a base 298 and a neck region 300 projecting upward from the base to ball member 294. The neck region may be sized to extend through aperture 296, with the diameter of the aperture substantially greater than that of the neck region. Accordingly, the neck region can travel laterally in aperture 296, which produces transverse motion 120 of floating articular member 282 with respect to the fixed portions of the prosthesis. Base 298 may be too wide to fit through aperture 296, which traps support member 288 in cup member 76. Base 298 may slide transversely (in this case, translationally) on a floor 302 of the cup member to form a movable planar joint 304. Floor 302 may be formed by a polymer insert or liner 306 disposed at the bottom of a recess defined by a metal portion of the cup member.

Example 5

Prosthesis with a Dish Member that Slides and Rocks

Figure 20:
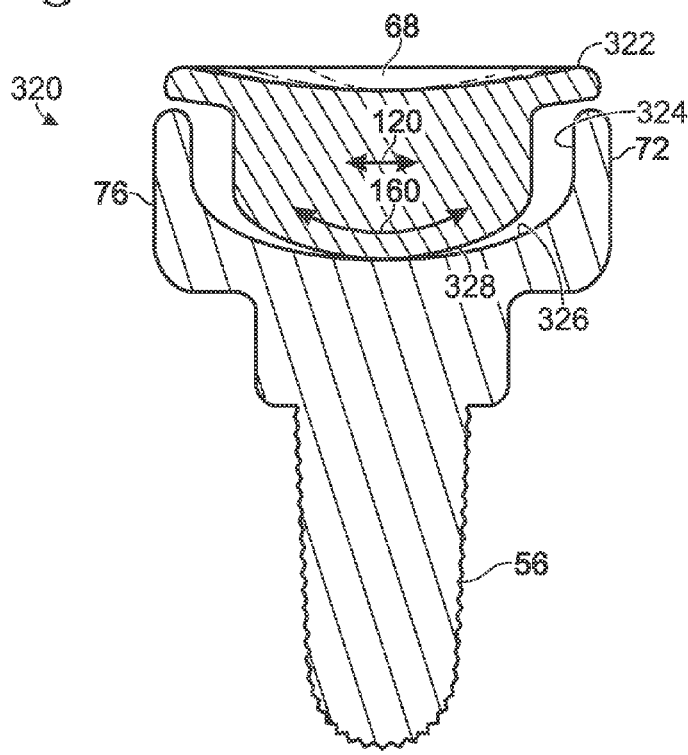
FIG. 20 is a sectional view of a ninth embodiment of a radial head prosthesis having a floating articular member, with the articular member having a convex bottom surface that is slidably engaged with a concave floor region of a cup member, in accordance with aspects of the present disclosure.

This example describes exemplary prostheses having a slidable dish member that is capable of sliding and/or rocking motion on various cup member surface regions; see FIGS. 20-22.

FIG. 20 shows a radial head prosthesis 320 having a slidable dish member 322 for engagement with the capitellum. Prosthesis 320 has a cup member 76 defining a recess 324 having a concave floor region 326. The floor region may be curved in a concave manner (e.g., spherical), and may be coaxial with articular surface region 72 of the cup member and/or the articular surface of the capitellum, when the dish member is in use. Floor region 326 may be slidably engaged with a convex underside 328 of dish member 322. Underside 328 may be spherical, with a smaller radius than floor region 326 of the cup member. Accordingly, dish member 322 can undergo transverse motion 120 along a curved path defined by floor region 326 and can undergo rotational motion 160 by rocking/rolling from side to side on floor region 326. Dish member 322 may (or may not) be trapped in cup member 76 with a retainer. In other embodiments, floor region 326 may be planar, and underside 328 still may be convex, such as spherical.

FIG. 21 shows a radial head prosthesis 340 having a slidable dish member 342 for engagement with the capitellum. The dish member has a flat bottom surface region 344 that is slidably engaged with a flat floor region 346 of a cup member 76. Dish member 342 can undergo transverse motion 120 at a planar joint 348. The dish member may or may not be trapped in cup member 76.

FIG. 22 shows another radial head prosthesis 360 having a slidable dish member 362 for engagement with the capitellum. The dish member has a spherical concave bottom surface region 364 that is slidably engaged with a complementary, spherical floor region 366 of a cup member 76, to permit transverse motion 120. Dish member 362 can slide along curved floor region 366, which may have the same radius as concave surface region 364 of the dish member. In other embodiments, floor region 364 may be provided by a retainer that attaches the dish member to the cup member.

Example 6

Prosthesis with a Dish Member Received Transversely

This example describes an exemplary prosthesis 380 having a floating dish member 54 received transversely during assembly of the prosthesis; see FIG. 23.

Prosthesis 380 has a head portion 52 composed of dish member 54 for articulation with the capitellum, a body or housing member 382, and a door or cap member 384. Body member 382 is analogous to cup member 76 of prosthesis 50 (e.g., see FIGS. 4 and 7). The body member may be configured to engage a stem component 84 of the prosthesis, to fix the body member to the stem component. Body member 382 may have a side articular surface region 72 for articulation with the radial notch of the ulna.

Body member 382 may define a cavity 386 sized to receive a base region 106 of the dish member. Cavity 386 may provide an entryway or mouth 388 on a side region of body member 382, which allows dish member 54 to be placed transversely into the cavity. Door member 384 may be attachable to body member 382, to close the lateral entryway to cavity 386, thereby trapping the base of the dish member in the cavity. Door member 384 may be attached to body member 382 by any suitable fastening mechanism, such as a pair of clips 390 that engage body member 382.

In the depicted embodiment, the upper region of dish member 54 is disposed above body member 382, after the prosthesis is assembled. In other embodiments, body member 382 may be structured as a cup member capable of receiving a majority of the upper region of dish member 54. For example, in the assembled prosthesis, dish member 54 may not project substantially (or at all) above the top of body member 382.

Example 7

Prosthesis with a Dish Member Retained by a Clip

This example describes an exemplary prosthesis 400 having a slidable dish member 402 held in a cup member 76 by a clip 404; see FIGS. 24 and 25.

Clip 404 may be generally C-shaped (e.g., a split ring) with a gap 406 that permits the clip to be placed around dish member 402. The gap also allows the clip to be compressed to a smaller diameter, for placement of the clip into the cup member, below an overhanging lip or flange 408 thereof. Clip 404 then can expand resiliently back to a larger diameter, to trap dish member 402 in cup member 76. Clip 404 may be received in a circumferential groove 410 defined by a side wall of dish member 402. Groove 410 may be deep enough to receive a greater portion of clip 404 when the clip is compressed. Clip 404 may have a bevel 412 that functions to urge the clip radially inward, deeper into groove 410, when the dish member is being urged downward into the cup member during assembly of the head portion. Cup member 76 may have a polymer liner 414 to facilitate sliding of dish member 402 against the cup member and/or to reduce swarf, among others.

Example 8

Prosthesis with a Dish Member Retained by a Pin

This example describes an exemplary prosthesis 420 having a floating dish member 422 held in a cup member 76 by a pin 424; see FIGS. 26 and 27.

Pin 424 may be placed through an opening defined by a side wall region of cup member 76 and into a slot 426 defined by dish member 422. The relative size, geometry, and position of the pin and slot may determine the permitted range of motion for dish member 422. For example, the dish member may be permitted to undergo transverse motion 120 by sliding, and, optionally, rotational motion 160 by rocking. The dish member (and/or a floor region 428 of cup member 76) may have a curved (e.g., spherical) surface region 430 that facilitates rotation by rocking (a rolling motion). Cup member 76 may (or may not) have a polymer liner 432.

Example 9

Prostheses with a Floating Head Member

This example describes exemplary prostheses having a floating head member 214 that articulates with both the humerus and the ulna; see FIGS. 28-31.

FIG. 28 shows a radial head prosthesis 440 having a stem assembly 442 that is connectable a head portion 52 of the prosthesis. Stem assembly 442 may include a base 444 that provides stem portion 56 and a mounting member 446 that mates with the base. The mounting member may define a support member 448 disposed above stem portion 56 and sized to be movably trapped in head portion 52.

Head portion 52 may include head member 214 and a pair of polymer liners 450 and 452. Head member 214 provides articular surface regions 68 and 72, and may be described as a dish member and/or an inverted cup member. The head member may be attached to polymer liners 450, each of which may be snap-locked in place.

Head portion 52 may be slidably connected to mounting member 446 of stem assembly 442. A support member 448 of the mounting member may be received and trapped in a cavity defined collectively by the head portion and a shoulder region 454 of base 444 of the stem assembly. The relative sizes of support member 448 and the cavity may determine the range of permitted motion for head portion 52 and/or head member 214.

Head member 214, mounting member 446, and liners 450 and 452 may be pre-assembled to form a head assembly including head portion 52, with a shaft 456 of mounting member 446 projecting from the underside of the head portion. The head assembly may be attached to base 444, such as by mating, to form the complete prosthesis.

Head portion 52 and/or head member 214 may float with respect to the stem portion. More particularly, the head portion/member may be free to undergo transverse motion 120 and rotational motion 160 at a same joint 458. For example, the head portion may rock on a curved (e.g., spherical) surface region 460 of support member 448, to change the tilt of the head portion with respect to the stem portion.

FIG. 29 shows another radial head prosthesis 480 having a stem component 482 that is operatively connectable to a floating head portion 52 of the prosthesis. The stem component may be structured generally like stem assembly 442 (see FIG. 28) except that the stem component may be only one piece. A support member 448 of the stem component may be trapped in head portion 52. During assembly, a resilient liner 484 may be placed onto support member 448, and then the liner and support member placed into a cavity 486 defined by head member 214. The head member may have at least one detent 488 to prevent removal of liner 484 from cavity 486. Head portion 52 and/or head member 214 may be free to undergo transverse motion 120 and rotational motion 160 in the assembled prosthesis, as described above for prosthesis 440 (see FIG. 28).

FIG. 30 shows yet another radial head prosthesis 500 having a stem component 502 that is operatively connectable to a floating head portion 52 (head member 214) of the prosthesis. Stem component 502 may include a base member 504 that forms stem portion 56, and a polymer cap 506 attached to an upper region of the base member. An enlarged top portion of stem component 502 may be received in a cavity 486 defined by head member 214. A retainer 508, such as a clip (e.g., a split ring), may be installed to capture the top portion of the stem component in head member 214. Retainer 508 may be received in a circumferential recess 510 defined inside head member 214. Retainer 508 may have an inclined surface region 512 that causes the retainer to be expanded radially outward, deeper into recess 510, as the top portion of the stem component is being forced into head member 214, past retainer 508.

Figure 31:
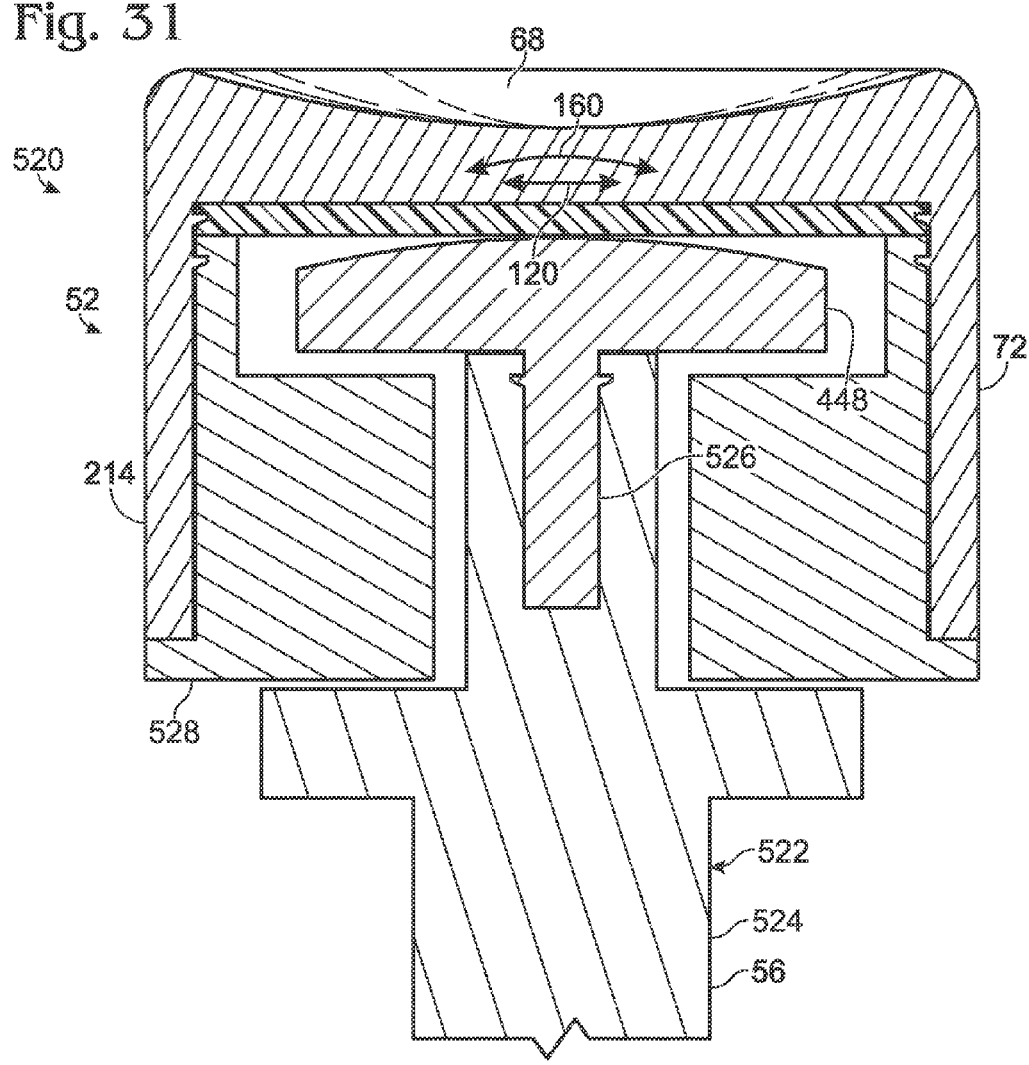
FIG. 31 is a fragmentary sectional view of an eighteenth embodiment of a radial head prosthesis having a floating articular member, in accordance with aspects of the present disclosure.

FIG. 31 shows yet another radial head prosthesis 520 having a stem component 522 that is operatively connectable to a floating head portion 52 of the prosthesis. Stem component may include a base member 524 that provides stem portion 56, and a mounting member 526 that provides support member 448. The support member may be trapped in the head portion by a retainer 528.

Example 10

Selected Embodiments 1

This example describes selected embodiments of a radial head prosthesis with a slidable head portion and/or a slidable articular member of the head portion, and methods of using the prosthesis. The selected embodiments are presented as a series of numbered paragraphs.

1. A method of repairing an elbow joint, the method comprising: (A) selecting a prosthesis including a head portion operatively connected or operatively connectable to a stem portion such that the head portion, and/or an articular member thereof, is slidable transversely to a long axis defined by the stem portion; and (B) installing the prosthesis such that the prosthesis is mounted to a radial bone and the head portion articulates with an ulnar bone and a humeral bone.

2. The method of paragraph 1, wherein the step of installing includes a step of disposing the stem portion in the radial bone.

3. The method of paragraph 1 or 2, further comprising a step of operatively connecting the head portion and/or the articular member to the stem portion during a surgical procedure.

4. The method of paragraph 3, wherein the step of operatively connecting is performed after the stem portion is disposed in the radial bone.

5. The method of paragraph 1, wherein the head portion includes a first articular member that articulates with the ulnar bone and a second articular member that articulates with the humeral bone, and wherein the first and second articular members are discrete and movable relative to one another with the head portion operatively connected to the stem portion.

6. The method of paragraph 5, wherein, with the head portion operatively connected to the stem portion, the first articular member is fixed with respect to the stem portion and the second articular member is movable with respect to the stem portion.

7. The method of paragraph 5 or 6, wherein the first articular member includes a cup member.

8. The method of paragraph 7, wherein the second articular member is disposed in the cup member.

9. The method of any of paragraphs 1 to 8, wherein the head portion and/or the articular member is slidable along a linear path with respect to the stem portion.

10. The method of any of paragraphs 1 to 9, wherein the head portion and/or the articular member is slidable along a curved path with respect to the stem portion.

11. The method of paragraph 10, wherein curved path is defined by at least one spherical surface region.

12. The method of any of paragraphs 1 to 11, wherein head portion includes a top articular surface region to contact the capitellum and a side articular surface region to contact the radial notch, and wherein the top articular surface region is movable with respect to the side articular surface region.

13. The method of paragraph 12, wherein the side articular surface region is fixed with respect to the stem portion, and wherein the top articular surface region is movable transversely with respect to the stem portion.

14. The method of paragraph 12 or 13, wherein the top articular surface region is spherical.

15. The method of any of paragraphs 12 to 14, wherein the top articular surface region is provided by an articular member that is spring-biased.

16. The method of paragraph 15, wherein the stem portion defines a long axis, and wherein the articular member is spring-biased along an axis that is at least generally parallel to the long axis.

17. The method of any of paragraphs 12 to 16, wherein the prosthesis is installed in a recipient, wherein the top articular surface region has a radius of curvature and is provided by first articular member, wherein the side articular surface region is provided by a second articular member, further comprising a step of selecting the first articular member from a set of two or more first articular members having different radii of curvature, and a step of operatively connecting the selected first articular member to the second articular member.

18. The method of paragraph 17, wherein the second articular member has a diameter, further comprising a step of selecting the second articular member from a set or two or more second articular members having different diameters.

19. A method of repairing an elbow joint, the method comprising: (A) selecting a prosthesis including a head portion having a first articular member and a second articular member that are discrete from one another, the head portion being operatively connected or operatively connectable to a stem portion with the first and second articular members are movable relative to one another in the absence of bone; and (B) installing the prosthesis such that the prosthesis is mounted to a radial bone, the first articular member articulates with an ulnar bone, and the second articular member articulates with a humeral bone.

20. The method of paragraph 19, wherein the first articular member is fixed with respect to the stem portion when the head portion is operatively connected to the stem portion.

21. The method of paragraph 19 or 20, wherein the first articular member includes a cup member, and wherein the second articular member includes a dish member.

22. The method of paragraph 21, wherein the dish member is disposed in the cup member when the head portion is operatively connected to the stem portion.

23. The method of paragraph 21 or 22, wherein the dish member is slidable transversely to a long axis defined by the stem portion when the head portion is operatively connected to the stem portion.

24. The method of any of paragraphs 21 to 23, wherein the second articular member has a spring-biased position with respect to the first articular member.

25. The method of paragraph 24, wherein the position of the second articular member is spring-biased along an axis that is at least generally parallel to a long axis defined by the stem portion.

26. The method of any of paragraphs 19 to 25, wherein the second articular member is pivotable with respect to the first articular member.

27. The method of any of paragraphs 19 to 26, wherein the second articular member is connected to the first articular member by a retainer received in a cup region of the first articular member.

28. The method of paragraph 27, further comprising a step of snap-fitting the retainer in the cup region such that the retainer is prevented from removal.

29. The method of paragraph 27 or 28, wherein retainer includes at least two discrete pieces that each receives a portion of the second articular member.

30. The method of paragraph 27, wherein the retainer includes a fastener that extends from an opening defined by the first articular member into an opening defined by the second articular member.

31. A prosthesis for elbow repair, comprising: (A) a stem portion configured to be received in a radial bone; and (B) a head portion including a first articular region configured to articulate with an ulnar bone and a second articular region configured to articulate with a humeral bone, the head portion being operatively connected or operatively connectable to the stem portion such that the first articular region, the second articular region, or both the first and second articular regions are slidable transversely to a long axis defined by the stem portion.

32. A prosthesis for elbow repair, comprising: (A) a stem portion configured to be received in a radial bone; and (B) a head portion including a first articular region configured to articulate with an ulnar bone and a second articular region configured to articulate with a humeral bone, the head portion being operatively connected or operatively connectable to the stem portion such that the first articular region is fixed with respect to the stem portion and the second articular region is slidable transversely to a long axis defined by the stem portion.

33. The prosthesis of paragraph 32, wherein the second articular region has a spring-biased position with respect to the first articular region.

34. A system for elbow repair, comprising: (A) a stem portion; (B) a first articular member operatively connected or connectable to the stem portion and configured to articulate with a radial notch of an ulnar bone; and (C) a second articular member configured to be slidably connected to the first articular member and to articulate with a capitellum of a humeral bone.

35. The system of paragraph 34, further comprising a set of first articular members that includes the first articular member, each first articular member being operatively connected or connectable to a stem portion and each having a different diameter.

36. The system of paragraph 35, wherein each first articular member is operatively connectable to a same stem portion.

37. The system of paragraph 35, wherein each first articular member is included in a distinct pre-formed component that includes a stem portion.

38. The system of any of paragraphs 34 to 37, further comprising a set of second articular members that includes the second articular member, each second articular member being slidably connectable to the first articular member and each having an articular surface region with a different curvature.

39. The system of any of paragraphs 34 to 38, further comprising a retainer to slidably connect the second articular member to the first articular member.

40. The system of paragraph 39, wherein the first and second articular members are formed of metal and the retainer is formed of plastic.

41. The system of any of paragraphs 34 to 40, wherein the second articular member has a spring-biased position with respect to the first articular member when the second articular member is slidably connected to the first articular member.

Example 11

Selected Embodiments II

This example describes additional selected embodiments of a prosthesis with a slidable head portion and/or a slidable articular member of the head portion, and methods of using the prosthesis. The selected embodiments are presented as a series of numbered paragraphs.

A1. A method of replacing an end of a radial bone with a prosthesis having a fixed member and a floating member, the method comprising: installing the prosthesis such that the prosthesis is attached to a radial bone, the fixed member articulates with an ulnar bone, and the floating member articulates with a humeral bone.

A2. The method of paragraph A1, wherein at least one of the ulnar bone and the humeral bone includes a prosthetic region, and wherein at least one of the fixed member and the floating member articulates at least in part with a prosthetic region.

A3. The method of paragraph A1 or A2, wherein the fixed member includes a cup portion, and wherein a majority by volume of the floating member is disposed in the cup portion after the step of installing.

A4. The method of any of paragraphs A1 to A3, wherein the prosthesis includes a stem portion defining a long axis, and wherein the floating member is capable of moving as a unit transversely to the long axis during movement of the radial bone with respect to the ulnar bone and/or humeral bone after the step of installing.

A5. The method of any of paragraphs A1 to A4, wherein the floating member is capable of moving translationally during movement of the radial bone with respect to the ulnar bone and/or humeral bone after the step of installing.

A6. The method of any of paragraphs A1 to A5, wherein the floating member is rotatable with respect to the fixed member during movement of the radial bone with respect to the ulnar bone and/or humeral bone after the step of installing.

A7. The method of any of paragraphs A1 to A6, wherein the prosthesis includes a head portion that includes the fixed member and the floating member, and wherein the head portion includes at least one resilient member that is deformable to bias a position of the floating member with respect to the fixed member.

A8. A method of replacing a proximal end of a radial bone with a prosthesis having a stem portion and a head portion, the method comprising: installing the prosthesis in an operative configuration, with the stem portion mounted to a radial bone, a first member of the head portion articulating with an ulnar bone, a second member of the head portion articulating with a humeral bone, and the second member movably connected to the first member.

A9. The method of paragraph A8, wherein the stem portion defines a long axis, and wherein the first member and the second member are movable relative to each other in a direction transverse to the long axis during movement of the radial bone with respect to the ulnar bone and/or humeral bone after the step of installing.

A10. The method of paragraph A8 or A9, wherein the second member is movable translationally with respect to the first member in the operative configuration.

A11. The method of any of paragraphs A8 to A10, wherein the second member is rotatable with respect to the first member in the operative configuration.

A12. The method of any of paragraphs A8 to A11, wherein at least one of the ulnar bone and the humeral bone includes a prosthetic region, and wherein at least one of the first member and the second member articulates at least in part with a prosthetic region.

A13. The method of any of paragraph A8 to A12, wherein the second member is connected to the first member by a movable joint that permits translational motion and rotational motion of the first and second members relative to each other.

A14. The method of any of paragraphs A8 to A12, wherein the second member is connected to the stem portion by a slidable joint and a pivotable joint that are distinct from each other.

A15. A method of replacing a proximal end of a radial bone, the method comprising: installing a prosthesis, with a stem portion thereof mounted to a radial bone and an articular member of the prosthesis articulating with a humeral bone and operatively connected to the stem portion such that the articular member is permitted to float as a unit transversely to a long axis defined by the stem portion.

A16. The method of paragraph A15, wherein the step of installing disposes the articular member for articulation with an ulnar bone.

A17. The method of paragraph A15 or A16, wherein the articular member includes an inverted cup member that forms a first surface region for articulation with the humeral bone and a second surface region for articulation with the ulnar bone.

A18. The method of any of paragraphs A15 to A17, wherein step of installing permits the articular member to rotate as a unit with respect to the stem portion to change a tilt of the articular member with respect to the stem portion.

A19. The method of any of paragraphs A15 to A18, wherein the articular member is capable of moving translationally with respect to the stem portion while remaining operatively connected to the stem portion.

A20. The method of any of paragraphs A15 to A19, wherein the articular member is operatively connected to the stem portion by a movable joint including a spherical surface region corresponding to no more than one-half of a complete sphere.

B1. A device for replacing a proximal end of a radial bone, comprising: (i) a stem portion that mounts to a radial bone; and (ii) a head portion operatively connected or connectable to the stem portion and including a fixed member to articulate with an ulnar bone and a floating member to articulate with a humeral bone.

B2. The device of paragraph B1, wherein the fixed member includes a cup portion, and wherein a majority by volume of the floating member is disposed in the cup portion when the head portion is operatively connected to the stem portion.

B3. The device of paragraph B1 or B2, wherein the floating member defines a concave articular surface region on a top side of the head portion.

B4. The device of any of paragraphs B1 to B3, wherein the floating member is movable translationally while the head portion remains operatively connected to the stem portion and the stem portion remains stationary.

B5. The device of paragraph B4, wherein the floating member is movable in a plane that is transverse to a long axis defined by the stem portion while the head portion remains operatively connected to the stem portion and the stem portion remains stationary.

B6. The device of any of paragraphs B1 to B5, wherein the floating member is rotatable while the head portion remains operatively connected to the stem portion and the stem portion remains stationary.

B7. The device of any of paragraphs B1 to B6, wherein, when the head portion is operatively connected to the stem portion, the floating member is operatively connected to the fixed member to form a joint that permits translational motion and rotational motion of the floating member relative to the fixed member.

B8. The device of any of paragraphs B1 to B6, wherein the floating member is operatively connected to the stem portion by a first joint that permits transverse motion of the floating member with respect to the stem portion and by a second joint that permits pivotal motion of the floating member with respect to the stem portion.

B9. The device of any of paragraphs B1 to B8, wherein the head portion includes a resilient member that biases a position of the floating member relative to the fixed member.

B10. The device of any of paragraphs B1 to B9, wherein at least one of the fixed member and the floating member is configured to articulate at least in part with a prosthetic region of an ulnar bone or a humeral bone.

B11. A device for replacing a proximal end of a radial bone, comprising: (i) a stem portion that mounts to a radial bone; and (ii) a head portion operatively connected or connectable to the stem portion and including a first member to articulate with an ulnar bone and a second member to articulate with a humeral bone, the second member being movably connected to the first member when the head portion is operatively connected to the stem portion.

B12. The device of paragraph B11, wherein the second member is movable translationally with respect to the first member while the head portion remains operatively connected to the stem portion.

B13. The device of paragraph B11 or B12, wherein the second member is movable rotationally with respect to the first member while the head portion remains operatively connected to the stem portion.

B14. A device for replacing a proximal end of a radial bone, comprising: (i) a stem portion that mounts to a radial bone; and (ii) a head portion including an articular member for articulation with a humeral bone, the head portion being operatively connected or connectable to the stem portion such that the articular member is permitted to float as a unit relative to the stem portion and transversely to a long axis defined by the stem portion.

B15. The device of paragraph B14, wherein the articular member is configured to articulate with an ulnar bone.

C1. A method of replacing an end of a bone with a prosthesis having a fixed member and a floating member, the method comprising: installing the prosthesis such that the prosthesis is attached to a first bone, the fixed member articulates with a second bone, and the floating member articulates with a third bone.

C2. The method of paragraph C1, wherein at least one of the second and third bones includes a prosthetic region, and wherein at least one of the fixed member and the floating member articulates at least in part with a prosthetic region.

C3. The method of paragraph C1 or C2, wherein the fixed member includes a cup portion, and wherein a majority by volume of the floating member is disposed in the cup portion after the step of installing.

C4. The method of any of paragraphs C1 to C3, wherein the prosthesis includes a stem portion defining a long axis, and wherein the floating member is capable of moving as a unit transversely to the long axis during movement of the first bone with respect to the second bone and/or third bone after the step of installing.

C5. The method of any of paragraphs C1 to C4, wherein the floating member is capable of moving translationally during movement of the first bone with respect to the second bone and/or third bone after the step of installing.

C6. The method of any of paragraphs C1 to C5, wherein the floating member is rotatable with respect to the fixed member during movement of the first bone with respect to the second bone and/or third bone after the step of installing.

C7. The method of any of paragraphs C1 to C6, wherein the prosthesis includes a head portion that includes the fixed member and the floating member, and wherein the head portion includes at least one resilient member that is deformable to bias a position of the floating member with respect to the fixed member.

C8. A method of replacing an end of a bone with a prosthesis having a stem portion and a head portion, the method comprising: installing the prosthesis in an operative configuration, with the stem portion mounted to a first bone, a first member of the head portion articulating with a second bone, a second member of the head portion articulating with a third bone, and the second member movably connected to the first member.

C9. A method of replacing an end of a bone, the method comprising: installing a prosthesis, with a stem portion thereof mounted to a first bone and an articular member of the prosthesis articulating with a second bone and operatively connected to the stem portion such that the articular member is permitted to float as a unit transversely to a long axis defined by the stem portion.

C10. The method of paragraph C9, wherein the articular member is rotatable with respect to the stem portion.

C11. The method of paragraph C9, wherein the articular member articulates with a second bone and a third bone.

C12. The method of any of paragraphs C9 to C11, wherein the articular member is operatively connected to the stem portion by a movable joint including a spherical surface region forming less than one-half of a complete sphere.

D1. A device for replacing an end of a bone, comprising: (i) a stem portion that mounts to a first bone; and (ii) a head portion operatively connected or connectable to the stem portion and including a fixed member to articulate with second bone and a floating member to articulate with a third bone.

E1. A device for replacing an end of a bone, comprising: (i) a stem portion that mounts to a first bone; and (ii) a head portion operatively connected or connectable to the stem portion and including a first member to articulate with a second bone and a second member to articulate with a third bone, the second member being movably connected to the first member when the head portion is operatively connected to the stem portion.

F1. A device for replacing an end of a bone, comprising: (i) a stem portion that mounts to a first bone; and (ii) a head portion including an articular member for articulation with a second bone, the head portion being operatively connected or connectable to the stem portion such that the articular member is permitted to float as a unit relative to the stem portion and transversely to a long axis defined by the stem portion.

F2. The device of paragraph F1, wherein the articular member is configured to articulate with a third bone.

The disclosure set forth above may encompass multiple distinct inventions with independent utility. Although each of these inventions has been disclosed in its preferred form(s), the specific embodiments thereof as disclosed and illustrated herein are not to be considered in a limiting sense, because numerous variations are possible. The subject matter of the inventions includes all novel and nonobvious combinations and subcombinations of the various elements, features, functions, and/or properties disclosed herein. The following claims particularly point out certain combinations and subcombinations regarded as novel and nonobvious. Inventions embodied in other combinations and subcombinations of features, functions, elements, and/or properties may be claimed in applications claiming priority from this or a related application. Such claims, whether directed to a different invention or to the same invention, and whether broader, narrower, equal, or different in scope to the original claims, also are regarded as included within the subject matter of the inventions of the present disclosure. Further, ordinal indicators, such as first, second, or third, for identified elements are used to distinguish between the elements, and do not indicate a particular position or order of such elements, unless otherwise specifically stated.

We claim:

1. A method of replacing an end of a radial bone with a radial head prosthesis having a stem portion and a head portion, the head portion connected or connectable to the stem portion, the head portion comprising a fixed member and a floating articular member, the method comprising:
   operatively installing the prosthesis such that the stem portion of the prosthesis is attached to a radial bone, the fixed member directly articulates with an ulnar bone, and the floating articular member directly articulates with a humeral bone and is operatively movable translationally with respect to the fixed member in a direction transverse to a long axis defined by the radial bone when the radial head prosthesis is finally implanted and fully operational,
   wherein the fixed member includes a cup portion, and wherein the floating articular member is disposed in the cup portion after the step of installing.

2. The method of claim 1, wherein at least one of the ulnar bone and the humeral bone includes a prosthetic region, and wherein at least one of the fixed member and the floating member articulates at least in part with a prosthetic region.

3. The method of claim 1, wherein a majority by volume of the floating member is disposed in the cup portion after the step of installing.

4. The method of claim 1, wherein the floating member is rotatable with respect to the fixed member during movement of the radial bone with respect to the ulnar bone and/or humeral bone after the step of operatively installing.

5. The method of claim 1, wherein wherein the head portion includes at least one resilient member that is deformable to bias a position of the floating member with respect to the fixed member.

6. A method of replacing a proximal end of a radial bone with a radial head prosthesis having a stem portion and a head portion, the head portion connected or connectable to the stem portion, the method comprising:
installing the prosthesis in an operative configuration, with the stem portion mounted to a radial bone, a first member of the head portion directly articulating with an ulnar bone and fixed with respect to the stem portion, and a second member of the head portion directly articulating with a humeral bone and operatively movable translationally with respect to the first member in a direction transverse to a long axis defined by the stem portion when the radial head prosthesis is finally implanted and fully operational,
wherein the second member is a floating articular member, wherein the first member includes a cup portion, and wherein the floating articular member is disposed in the cup portion after the step of installing.

7. The method of claim 6, wherein the second member is rotatable with respect to the first member in the operative configuration.

8. The method of claim 6, wherein at least one of the ulnar bone and the humeral bone includes a prosthetic region, and wherein at least one of the first member and the second member articulates at least in part with said prosthetic region.

9. The method of claim 6, wherein the second member is connected to the first member by a movable joint that permits translational motion and rotational motion of the first and second members relative to each other.

10. The method of claim 6, wherein the second member is connected to the stem portion by a slidable joint and a pivotable joint that are distinct from each other.

11. The method of claim 6, wherein the step of installing permits the floating articular member to rotate as a unit with respect to the stem portion to change a tilt of the floating articular member with respect to the stem portion.

12. The method of claim 6, wherein the floating articular member is operatively connected to the stem portion by a movable joint including a spherical surface region corresponding to no more than one-half of a complete sphere.

\* \* \* \* \*